United States Patent
Losken et al.

[11] Patent Number: 6,033,412
[45] Date of Patent: Mar. 7, 2000

[54] AUTOMATED IMPLANTABLE BONE DISTRACTOR FOR INCREMENTAL BONE ADJUSTMENT

[76] Inventors: H. Wolfgang Losken, 4700 Ellsworth Ave. #14, Pittsburgh, Pa. 15213; Gerald G. Cano, 157 Crescent Hills Rd., Pittsburgh, Pa. 15235; Richard J. Arnott, 113 Hodil Ter., Pittsburgh, Pa. 15238; Thomas G. Loebig, 300 Rose Ave., Pittsburgh, Pa. 15235; David W. Smith, 609 Braddock Ave., Apt. #2, Pittsburgh, Pa. 15221

[21] Appl. No.: 09/054,657

[22] Filed: Apr. 3, 1998

Related U.S. Application Data

[60] Provisional application No. 60/042,677, Apr. 3, 1997.

[51] Int. Cl.[7] .................................................. A61B 17/66
[52] U.S. Cl. .............................. 606/105; 606/57; 606/60; 606/78
[58] Field of Search ................... 606/78, 76, 71, 606/70, 69, 62, 63, 64, 57, 58, 73

[56] References Cited

U.S. PATENT DOCUMENTS

| | | | |
|---|---|---|---|
| 5,415,660 | 5/1995 | Campbell et al. | 606/62 |
| 5,505,733 | 4/1996 | Justin et al. | 606/63 |
| 5,536,269 | 7/1996 | Spievcak | 606/60 |
| 5,575,790 | 11/1996 | Chen et al. | 606/60 |
| 5,626,581 | 5/1997 | Staehlin et al. | 606/63 |
| 5,720,746 | 2/1998 | Soubeiran | 606/61 |
| 5,766,004 | 6/1998 | Besselink et al. | 433/5 |
| 5,782,713 | 7/1998 | Jobe | 606/69 |

*Primary Examiner*—Michael Buiz
*Assistant Examiner*—David O. Reip
*Attorney, Agent, or Firm*—Webb Ziesenheim Logsdon Orkin & Hanson, P.C.

[57] ABSTRACT

An implantable distractor that provides controlled forceful movement either to facing bone ends created by osteotomy or across cranial sutures for the purpose of fostering bone deposition to support bone growth (distraction osteogenesis). The improved Distractor adjusts separation of such through precise, forceful, incremental movements. The mechanism has an actuator powered by intermittent electrical current flow through a shape-memory-effect (SME) actuation component. The SME component deforms forcefully. This force is amplified to result in incremental separation of two plates affixed to bone on either side of the osteotomy or suture.

21 Claims, 16 Drawing Sheets

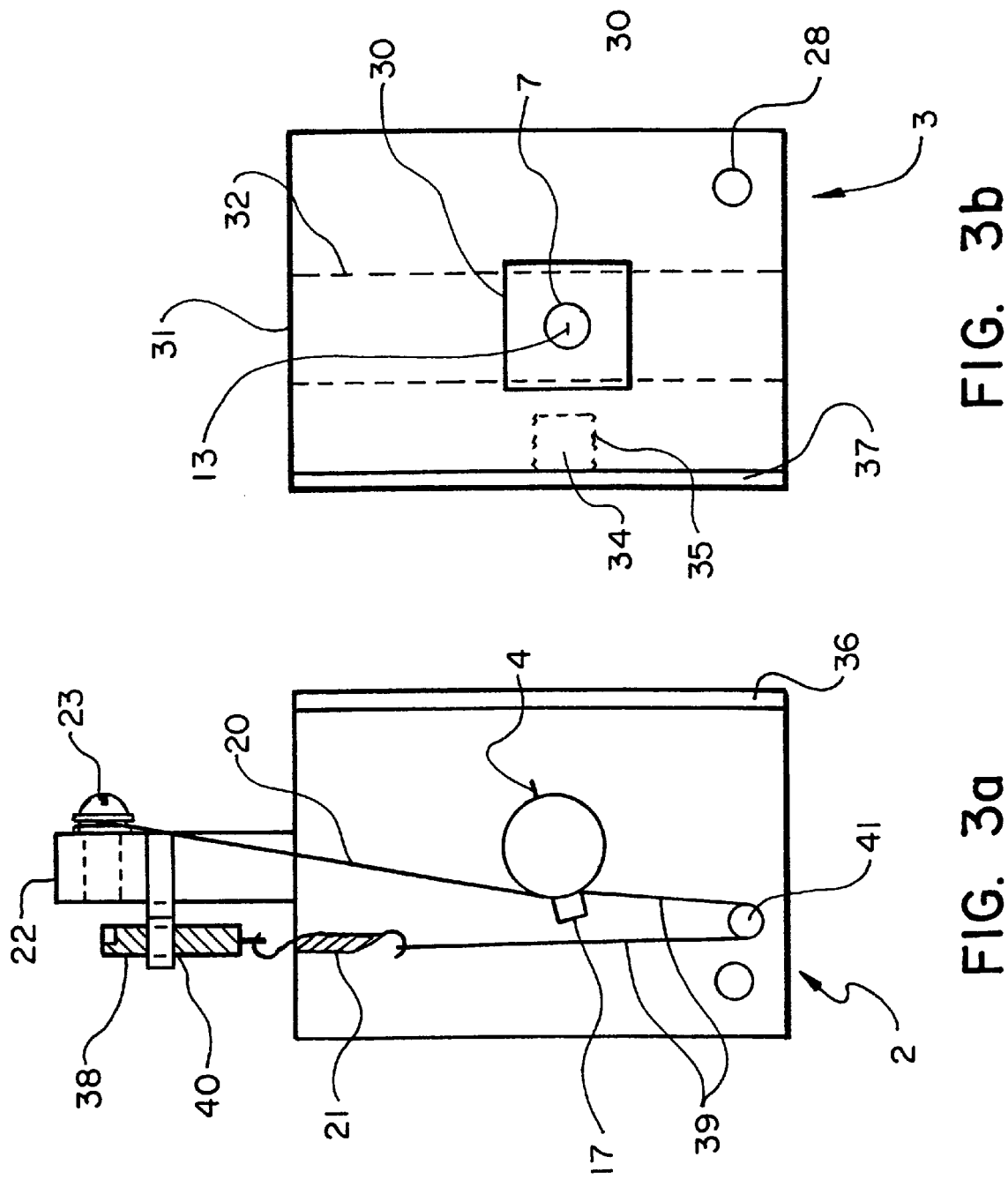

DIRECTION OF ROTATION

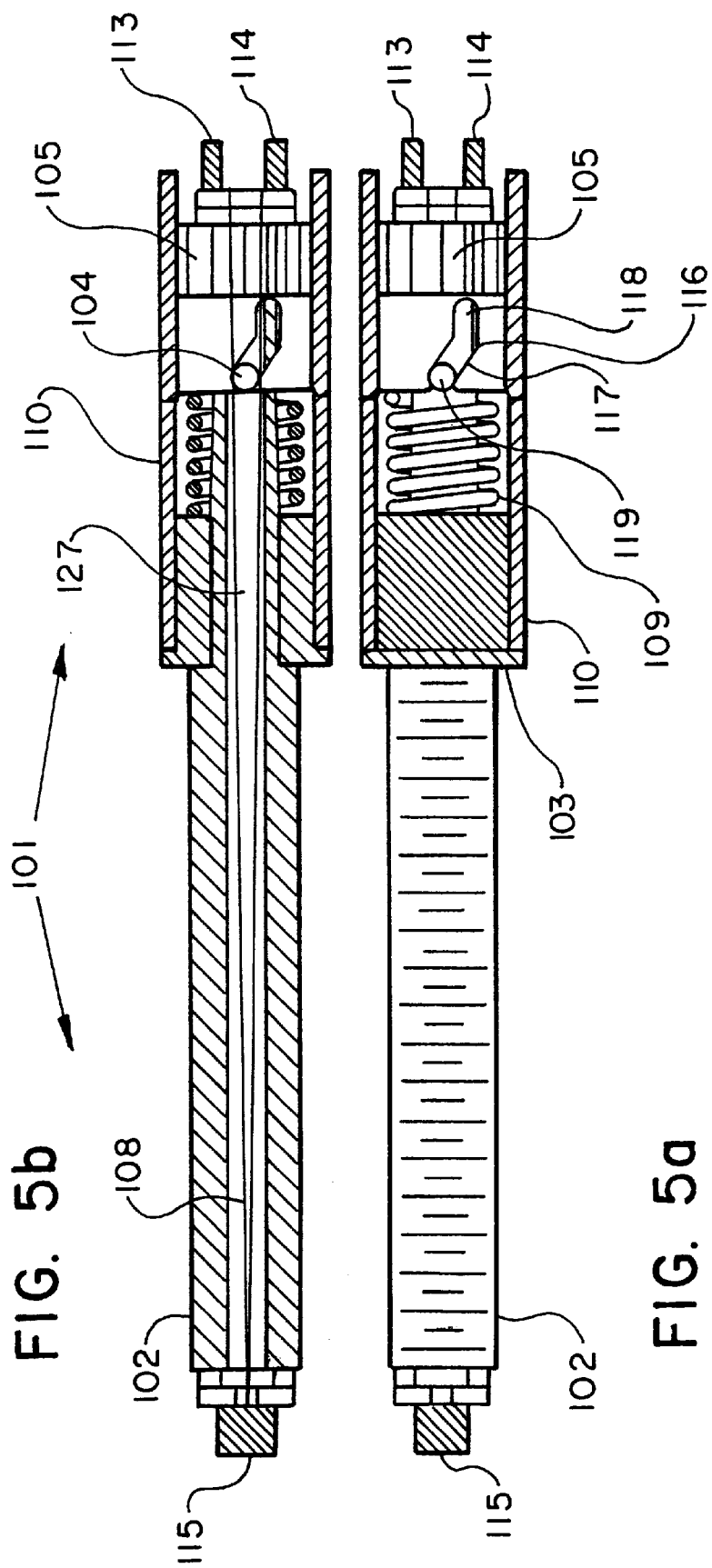

AUTOMATED IMPLANTABLE BONE DISTRACTOR FOR INCREMENTAL BONE ADJUSTMENT

This application claims the benefit of co-pending U.S. Provisional Application Ser. No. 60/042,677 entitled "Nitinol Activated Bone Lengthening Device", filed on Apr. 3, 1997 which is incorporated herein by reference.

This invention was made with Government support under Grant No. 1-R43-AR44172-01 awarded by the National Institute of Arthritis, Musculoskeletal and Skin Disease. The Government has certain rights in the invention.

BACKGROUND OF THE INVENTION

1. Field of the Invention

The present invention relates to an implantable bone distractor, more particularly to an improved bone distractor to controllably separate facing bone ends, such as at osteotomies or across cranial sutures, relative to each other in a way to stimulate new bone deposition to alter bone geometry, distraction osteogenesis.

2. Background information

Distraction

Distraction osteogenesis is a process for forming new bone in sufficient quantity to measurably alter bone dimensions. It is accomplished by slow separation of bone ends at an osteotomy or suture to stimulate osteogenesis between the ends. The separation is followed by fixation for a sufficient period to enable the bone matrix to harden. This process can eliminate the need for bone grafts. The surrounding soft tissues, blood vessels and nerves lengthen to accommodate the modified bone geometry.

The technique of gradual distraction is now well understood in orthopedic surgery. Codivilla first described the process as applied to a femur in 1905 to correct a limb length deficiency. See Codivilla A, "On the means of lengthening, in the lower limbs, the muscles and tissues which are shortened through deformity", Am J Orthop Surg 2:353, 1905. In 1927, Abbott lengthened a tibia and fibula, as described in "The operative lengthening of the tibia and fibula", J Bone Joint Surg 9:128, but because of complications, the procedure was abandoned. In the 1950's, Gavriel A. Ilizarov, a Russian physician, routinely performed distraction osteogenesis in the human femur, tibia, radius, ulna, humerus, iliac crest and bones of the hands. See Ilizarov GA, "The principles of the Ilizarov method", Bull Hosp Joint Dis Orthop Inst Paley, 48:1, 1988; Ilizarov GA. "The tension-stress effect on the genesis and growth of tissues, Part I: The influence of stability of fixation and soft tissue preservation", Clinical Orthopedics 238:249–281, 1989; and Ilizarov GA. "The tension-stress effect on the genesis and growth of tissues, Part II: The influence of the rate and frequency of distraction", Clinical Orthopedics, 239:263–285, 1989. Paley D., in "Problems, obstacles, and complications of limb lengthening by the Ilizarov Technique", Clin Orthop 250:81, 1990; Paterson D., in "Leg-lengthening procedures. A historical review", Clin Orthop 250:27, 1990, Villa et al., in "Lengthening of the forearm by the Ilizarov Technique", Clin Orthop 250:125, 1990, and Catteneo et al., in Lengthening of the Humerus Using the Ilzarov Technique. Clin Orthop 250:117, 1990 have also reported on their experiences. However, its clinical application remains limited by the state of Distractor design technology. Current devices in clinical use are external mechanisms that are attached to bone percutaneously by screws or rods, thus presenting a significant risk for infection and producing psychological trauma. Muscle contraction, joint luxation or stiffness, axial deviation, neurological and vascular injuries, consolidation problems and attachment site problems further complicate the procedure.

Distraction has shown potential in treating craniofacial growth deficits and mandibular deficiencies. Successful experimental distraction osteogenesis of the mandible has been described in dogs in Snyder et al., "Mandibular lengthening by gradual distraction", Plast and Reconstr Surg 51:506–508, 1973; Michieli and Miotti, "Surgical-orthodontic mandibular body lengthening by gradual distraction"; Minerva Stomatol 1976; Karp et al., "Bone lengthening in the craniofacial skeleton", Annals of Plastic Surgery 24: 231–237, 1990 and "Membranous bone lengthening: A serial histological study", Annals of Plastic Surgery 29:2–7, 1992; Constantino et al., "Distraction osteogenesis: Application for mandibular regrowth", Otolaryngologic Clinics of North America 24:1433–443, 1991, and "Experimental mandibular regrowth by distraction osteogenesis", Arch Otolaryngol Head Neck Surg 119: 511–516, 1993; McCarthy et al., "Lengthening the human mandible by gradual distraction", Plast Reconstr Surg 89:1–8, 1992; Block et al., "Changes in the inferior alveolar nerve following mandibular lengthening in the dog using distraction osteogenesis", J Oral Maxillofac Surg 51:652–660,1993; and Staffenberg et al., "Mandibular lengthening in the canine using an intraoral device", Fifth International Craniofacial Congress 5:77, 1993. See also Miller ME, Christensen GC, Evans HE., "The Anatomy of the Dog", WB Saunders, 1964. Successful experimental distraction osteogenesis of the mandible has also been described in sheep in Karaharju-Suvanto et al., "Mandibular distraction: An experimental study on sheep", J Cranio Max Fac Surg 18:280–183, 1990 and "Distraction osteogenesis of the mandible", J Oral Maxillofac Surg 21:118–121, 1992. In 1992, McCarthy et al., "Lengthening of the mandible by gradual distraction: Experimental and clinical studies", Craniofacial Surgery 4 p. 85–88, 1992, utilized an external bone distractor on the human mandible, fixed with double pins inserted into each bony segment through a lateral skin incision. Molina and Ortiz Monasterio, "Extended indications for mandibular distraction: unilateral, bilateral and bidirectional", International Craniofacial Congress 5:79, 1993 also reported human mandibular distraction but approached the mandible through a vestibular incision. They performed a corticotomy of the lateral surface of the mandible, fixing the distractor with a single pin in each bony segment. They also presented double bone osteotomies of the mandible on the same side, with single pin fixation in each of the three segments to differentially distract the vertical and horizontal rami. In 1995, Losken et al., "Geometric evaluation of mandibular distraction", The Journal of Craniofacial Surgery, 6:395–400, 1995, and "Planning mandibular distraction", Cleft Palate—Craniofacial Journal 32:71–76, 1995, reported on refinements in the apparatus, pin placement angulation, and mathematical modeling equations expected to improve the outcome of bilateral mandibular distraction using an external distraction device.

Distraction osteogenesis has also been used experimentally to correct growth deficits in the craniofacial skeleton. Persing et al., "Skull expansion in experimental craniosynostosis", Plast and Reconstr Surg 78:594–603, 1986, and "Skull base expansion: Craniofacial effects", Plast and Reconstr Surg 87:1028–1033, 1991, described the use of an implanted, uncontrollable spring distractor to expand the coronal suture and the cranial base, the frontosphenoidali suture, in rabbits with experimentally immobilized coronal sutures. Controllable, external distraction devices have also been utilized experimentally in the calvaria (Barone et al., "The frontal tiara", J Craniofac Surg (A3J) 3(3): 173–174, 1992.; Remmler et al., "Osseous expansion of the cranial vault by craniostasis", Plast Reconstr Surg 89: 787, 1992), the zygoma (Glat et al., "Multidimensional distraction osteogenesis: the canine zygoma", Plastic Reconstr Surg (P9S), 1994), and the midface (Rachmiel et al., "Midface advancement by gradual distraction", Br J Plast Surg (BOW) 46(3): 201–207, 1993). However, both implanted and external distractors continue to pose infection and scarring problems.

Cowan (citation omitted) also reported on growing fingers on children who were born without them. He has transplanted bone from the toes, divided them and distracted with an external rack.

Losken et al., (paper entitled "Internal Calverial Distraction in Rabbits with Delayed Onset Coronal Suture Synostosis", Plast Reconstr Surg, in press in conjunction with Karlsruhe Kern Institut in Germany, designed a totally implantable Distractor that was tested at the coronal suture in a rabbit model. The distractor, a screw-jack device, is manually adjusted subcutaneously with a screwdriver through repeated incision at the adjustment control site. Such adjustment is clinically unacceptable.

U.S. Pat. No. 5,505,733 to Justin et al. describes an Intramedullary Skeletal Distractor and Method. The Justin et al. patent discloses a pair of telescoping cylindrical members inserted into the intramedullary space of a bone that under normal torsion experienced by an affected limb, typically in the range of three to five degrees, causes the cylindrical members to be forced apart, separating the sections of bone. The Distractor limits distraction per unit time and provides a mechanism to allow initiation of a new cycle of elongation by forcible external manipulation. The device as described suffers from complex design. The method of activation by torsion of the limb is painful for the patient.

U.S. Pat. No. 5,415,660 to Campbell et al. describes an Implantable Limb Lengthening Nail Driven by a Shape Memory Alloy. The Campbell et al. patent discloses an intramedullary telescoping Distractor powered by a shape memory alloy element, preferably Nitinol. The shape memory element undergoes forceful dimensional change during heating resulting from electric current either passing through a heating element proximal to or in contact with the shape memory element or passing directly through the shape memory element causing Joule heating. Drive current is provided by an external signal to the adjustment mechanism. The preferred embodiment suffers from several shortcomings:

1) the design does not amplify the distraction force generated by the Nitinol;
2) without force amplification, the required Nitinol element must be relatively thick to generate adequate force for limb distraction so that either indirect heating or Joule heating is difficult and requires dissipation of large amounts of heat;
3) high internal frictional loss exacerbates force generation requirements placing further dimensional requirements on the Nitinol;
4) a cumbersome and difficult to manufacture ratchet system whose performance is challenged by the fine adjustment requirements needed for clinical distraction; and
5) as the tubular sections slide to expand the length, the housing volume increases so that internal pressure becomes sub-atmospheric, increasing the load and sucking body fluid into the device to possibly short electrical connections.

U.S. Pat. No. 5,536,269 to Spievack describes a Bone and Tissue Lengthening Device. Spievack discloses a hydraulically powered intramedullary device to enable continued bone growth. An operating fluid supply is implanted; it communicates with a piston and cylinder that drives a ratchet mechanism. A shock absorber mechanism reduces lost motion between piston and cylinder. Ratchet release means are employed to permit the piston and cylinder to reverse directions.

U.S. Pat. 5,575,790 to Chen et. al. describes a Shape Memory Alloy Internal Linear Actuator for Use in Orthopedic Correction in the form of a one-way rotatable clutch and screw combination, the clutch turned by a shape memory alloy actuator powered by the application of heat, the whole mechanism housed in a first tubular section and a second tubular section slidably received in telescoping relationship. The invention is deficient in that, as the tubular sections slide to expand the length of the device, the volume of the housing increases so that pressure within the housing becomes sub-atmospheric. As such, the load on the actuator can increase. Also, the device tends to suck body fluids into the device that can cause mechanical and electrical problems. The patent refers to the use of a Torrington Inc. roller clutch, Model No. R C-02 in the device. This clutch from Torrington, Inc., the leader in the roller clutch market, is the smallest such clutch available. Use of this type of mechanism can cause problems due to slipping as follows. The device described in the Chen et al. patent is designed to produce small rotational increments. Under load, such small clutches due to dimensions of parts tend to distort. The distortion leads to slippage which can exceed the degree of powered rotation. Consequently, the screw does not turn and the device does not lengthen.

U.S. Pat. 5,626,581 to Staehlin et al., describes an Implantable Bone Lengthening Apparatus in the form of an intramedullary nail which includes a shape-memory-material powered hydraulic pump, a shape-memory-material powered ratchet mechanism, a permeable head piston mechanism and a bellows extension mechanism. The device is complicated in design and uses shape-memory-material (Nitinol) in a spring configuration, which enables it to provide a significant drive stroke, but does not optimize the force producing capability of the Nitinol involved. The system does seek to amplify the drive force generated by the shape-memory-material (Nitinol) spring using recognized hydraulic principles. The patent also discloses an embodiment, again in the form of an intramedullary nail, which includes a reciprocating ratchet mechanism powered by a shape memory spring (Nitinol). The ratchet mechanism uses buttress arms contained in a cylinder with annular rings of a mating buttress shape machined into its wall. Movement is created by a shape-memory-material actuator consisting of a shape-memory-material (Nitinol) spring heated by an electrical heating element and biased by a return spring. The system suffers from inefficiencies similar to those of the device disclosed in the Campbell et al. patent. Specifically, the system does not seek to amplify forces generated by the shape-memory-material spring, the net force being reduced by high internal friction, thus restricting the ability to overcome resisting physiological forces.

A need exists in the art for a small, implantable distractor that is convenient to operate/control in the clinical setting; it should reduce both infection risks and scarring compared to an external distractor and also minimize both physical and psychological trauma to the patient. It must produce incremental adjustment in the separation of bone ends. In summary of the above-described devices, the clinical potential offered by distraction osteogenesis has been largely untapped due to lack of a clinically suitable distractor. Such a distractor must be implantable, small, and easily controlled. Nitinol's mechanical properties appropriately mesh with constraints imposed by these design requirements.

Nitinol, a shape-memory-effect alloy

Nitinol, an alloy of nickel and titanium, was invented in 1963 at the Naval Ordinance Laboratory. Since its discovery, metallurgical problems have impeded development of applications incorporating the alloy. Recently, however, these problems have been largely overcome. Nitinol belongs to a general category of alloys called "shape-memory-effect" alloys, also referred to as SME alloys or SME materials. These are capable of the following:

1) undergoing a drastic shape change in response to a small temperature change;
2) generating a significant force level as during a shape change;
3) repeating this shape change/force generation cycle thousands of times; and
4) superelastic recovery, a material behavior that occurs during stress unloading in their elastic region. Nitinol derives these macroscopic characteristics from the response of its crystal lattice to both temperature and stress.

Nitinol is capable of undergoing "shape recovery," a temperature dependent process in which the molecular lattice undergoes a phase change from Martensite to Austenite. That is, an element of Nitinol can be taught to remember a shape, deformed in its Martensite phase, and then return to the learned shape via a temperature initiated transformation to the Austenite phase:

1) training the Nitinol element is accomplished via an annealing process at a temperature between 600 and 850 degrees Centigrade;
2) at a temperature that is below the Martensite finish temperature (Mf), the Nitinol element can be deformed and remains so;
3) as temperature is increased to the Austenite start temperature (As) the Nitinol element begins the phase transformation from Martensite to Austenite;
4) at the Austenite finish temperature (Af), the element is completely Austenitic returning the Nitinol element to its learned shape.

It is this crystal lattice change that returns the element to its learned shape. The temperature difference between Mf and Af can be designed to be as small as ten degrees Centigrade.

Nitinol actuator wire, used to generate repeated motion, reacts similarly. When the wire undergoes a heat induce phase change from Martensite to Austenite, it shortens as its cross-sectional area increases. When allowed to cool to below Mf, the wire can be stretched to its original length using a force that is, favorably, less than one-fourth that generated during shortening. The wire can be heated by an impulse of electric current. For a six mm wire with a 90 degree Centigrade transition temperature, the current pulse needed to heat the wire can be so short that no heat can be detected when touching the wire during application of the current pulse. For a given piece of wire, it is possible to repeat the shortening/lengthening process hundreds of thousands of times without a reduction of performance or breaking of the wire.

Nitinol also has a superelastic form. Superelasticity, also known as pseudoelasticity, is a material behavior that occurs during unloading in the elastic region of the Nitinol material. This material "phenomenon" is most apparent between the Austenite start temperature (As), the temperature at which Nitinol begins changing from Martensite to Austenite, and the Martensite by deformation temperature (Md), the maximum temperature that allows for the formation of stress-induced Martensite. The apparent elasticity of Nitinol is the result of the unstable nature of the stress-induced phase transformation to Martensite above the Austenite finish temperature (Af). Superelastic Nitinol can be deformed by applied stress that causes a stress induced Martensite phase. This phase is inherently unstable due to strong intermolecular crystalline structure within the alloy. As a result, when the stress is relieved, the Nitinol will preferentially return to Austenite and, as a consequence, recover or return to its original shape.

Nitinol Actuators

A Nitinol actuator operates on a heating and cooling cycle established by an electric current provided by a controller. Electro-resistive heating raises the temperature of the Nitinol component. During that part of the cycle when current is on, the temperature of the Nitinol component rises to slightly above its transition temperature. At this temperature, the alloy lattice undergoes a change from Martensite (a soft form of the alloy) to Austenite (a harder form of the alloy). This temperature change alters the dimensions of the Nitinol component to cause forceful motion. During that part of the cycle when current is off, the temperature of the component falls to below transition. The alloy gradually returns to its Martensite form. This facilitates resetting the initial dimensions of the Nitinol component either passively or actively. Passive reset uses the elastic properties of a properly sized distended spring that maintains a near constant bias force sufficient to facilitate resetting the initial dimensions of the Nitinol component. Active reset uses a second Nitinol component in place of the bias spring. The second component is electrically heated, while the first is cooling, to supply force to reset the length of the first component. Conversely, when the second Nitinol component is cooling, the first supplies force to reset the second component.

SUMMARY OF THE INVENTION

It is an object of this invention to provide a small implantable distractor that is easily operated in the clinical setting, that reduces the risk of infection and scarring, and that also minimizes both physical and psychological trauma to the patient. It is a further object of this invention to provide the physician finite incremental separation adjustments of facing bone ends across the osteotomy. It is a further object of this invention that bone ends be prevented from slipping back into proximity with each other and that, when maximum displacement has been achieved, the distractor be able to fix the position of the original bone ends for a sufficient period to allow solidification of new bone deposited during the distraction process.

The improved distractor is implantable within the body, positioned across bone ends or sutures and adjusts separation of such through precise, forceful, incremental movements. The mechanism for precise, forceful, incremental movement is an actuator powered by intermittent electrical current flow through a shape-memory-effect (SME) actuation component. The SME component deforms forcefully. This force is amplified to increment separation of two plates affixed to bone on either side of a suture or osteotomy. The implantable bone distractor according to the present invention may include a first base member adapted to be coupled to the bone to be distracted and a second base member adapted to be attached to the bone to be distracted at a position spaced across a separation in the bone from the coupling of the first base member, wherein the second base member is movably coupled to the first base member. The distractor may further include a moving mechanism for precise, incremental movement of the second base member relative to the first base member and an actuating mechanism within the moving mechanism to modify the length of the moving mechanism, wherein the actuating mechanism includes a shape-memory alloy wire at least partially extending along a longitudinal length of the distractor, which extends generally along the direction of distraction. The distractor of the present invention allows for a unique method of distraction according to the present invention.

The method of bone distraction simulating natural bone growth according to the present invention comprising the steps of: mounting an electrically powered automatic bone distractor across the portion of the bone to be distracted; dividing a daily distraction distance into a plurality of small incremental distances, each incremental distance being less than about 0.1 mm; and automatically activating the distractor at distinct times for each said incremental distance. The distractor of the present invention can distract in increments less than 0.02 mm, specifically about 0.015 mm. Therefore, the method of the present invention may use increments of between 0.01 mm and 0.02 mm.

These and other advantages of the present invention will be clarified in the Brief Description of the Preferred Embodiments wherein like reference numeral represent like elements throughout.

BRIEF DESCRIPTION OF THE DRAWINGS

FIGS. 3A and 3B are plan views of Distractor mounting brackets components of the distractor illustrated in FIG. 1;

FIG. 4C schematically illustrates the profile of a portion of the ratchet face shown in FIGS. 4A and 4B;

FIG. 5A is a side view of an in-line electromechanical screw mechanism incorporating a cylindrical cam-gear ratchet, with Nitinol wire positioned in a hollow in the center of the length of the partially threaded shaft that forms the basis of an implantable distractor according to a second embodiment of the present invention;

FIG. 5B is a sectional view of the in-line electromechanical screw mechanism illustrated in FIG. 5A;

DETAILED DESCRIPTION OF THE PREFERRED EMBODIMENTS

Under a Small Business Innovative Research Grant (SBIR) from the National Institutes of Health (NIH) to Metamorphic Surgical Devices, Inc, Gerald G. Cano, PhD., Principal Investigator, the force-displacement (stress-strain) characteristics of normal and partially synostosed coronal suture in a rabbit model was investigated. Experiments revealed that the force necessary to distract a partially synostosed suture the initial 0.4 mm is less than approximately ten pounds whereas the force required to distract a suture one millimeter is over 100 pounds. A "proof of concept" distractor was designed; it was powered by a microprocessor-controlled electronic power supply. An initial external Distractor, similar to the one in FIG. 1, used a Torrington, Inc. R C-02 clutch as Chen et al.; under load, the clutch distorted and slipped so that there was no net rotation of the screw. That is, slipping occurred while distracting a rabbit model with a coronal suture width increased by about 0.3 mm. While the exact load was not measured, it can be assumed to be about 10 pounds, as indicated from suture characteristics. This design used a 1.8 inch length of doubled Nitinol wire, substantially longer than Chen et al. indicates; the longer wire should have produced considerably more rotation of the roller clutch than Chen et al., yet the system failed due to slippage from stress induced distortion. Consequently, the clutch was replaced with a high resolution ratchet. Bench tests demonstrated that the maximum resistive force against which the device could distract was approximately 27 pounds. Over the course of two weeks, growth deficient rabbits with partially synostosed coronol sutures were distracted 2.8 mm to catch up to normal with a "proof of concept" distractor. Distraction conducted frequently in very small increments can be accomplished at relatively low force (ten pounds or less). Results imply that the suture characteristics reset.

Figure 1:
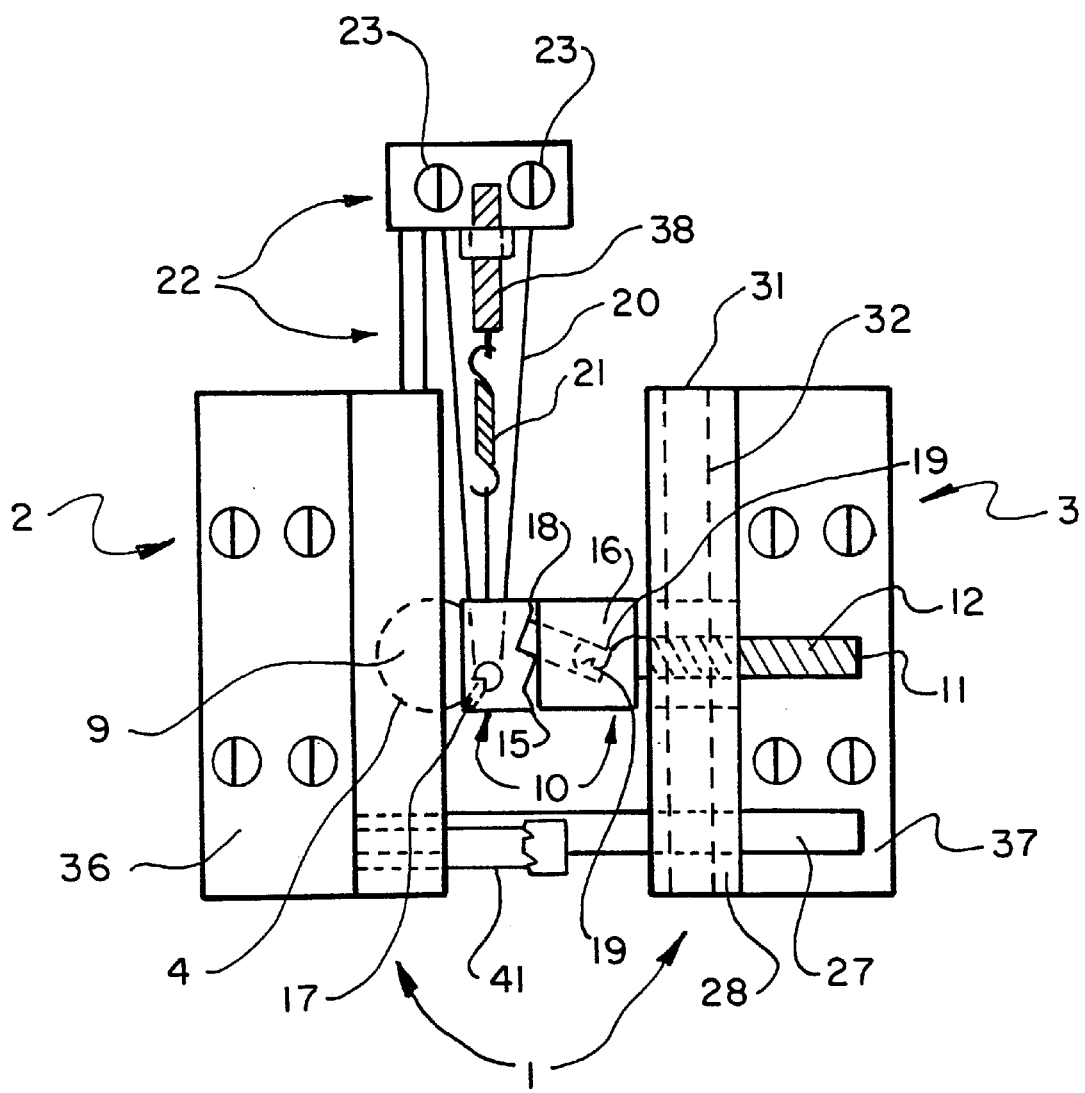
FIG. 1 is a schematic plan view of an externally mounted distractor according to a first embodiment of the present invention.

The "proof of concept" embodiment of a distractor 1 in accordance with the present invention is shown in FIG. 1. It is referred to as a "proof of concept" embodiment because the distractor 1 is not designed as an implantable device, but rather was designed to test and evaluate the operability of the components of the present invention. The external distractor 1 includes two brackets 2 and 3 that are affixed (secured) to flat plates 36 and 37, respectively, that are then screwed to bone, one each on either side of an osteotomy or cranial suture. Brackets 2 and 3 are shown in FIGS. 3A and B. Within bracket 2 is a socket 4 which is lined with plastic bearing surface 5. Within bracket 3 is slot 30 and blind hole 32. Rotating rod 31 is positioned in blind hole 32 so that threaded hole 7 in rod 31 is aligned with slot 30 and is free to rotate in blind hole 32. Ratchet and screw assembly 8, shown in FIG. 2, mount between brackets 2 and 3. Ratchet and screw assembly 8 consists of ball 9, ratchet 10 and screw 11. Ball 9 mates with bearing surface 5 in socket 4 which enables assembly to pivot relative to bracket 2. Threads 12 of screw 11 mate with threads 13 of hole 7. The pitch of threads 12 and 13 provide a predictable amount of linear travel by screw 11 through hole 7 per each revolution of screw 11 caused by the ratcheting action of ratchet 10. Brackets 2 and 3 separate an amount equal to linear travel of screw 11 through hole 7. Ball 9 in socket 4 and screw 11 in threaded hole 7 allow for vertical misalignment of brackets 2 and 3 when distractor 1 is screwed across an osteotomy or cranial suture. Ball 9 in socket 4 and blind hole 35 rotating on pivot 34 allow for horizontal misalignment of brackets 2 and 3 when distractor 1 is screwed across an osteotomy or cranial suture.

Figure 2:
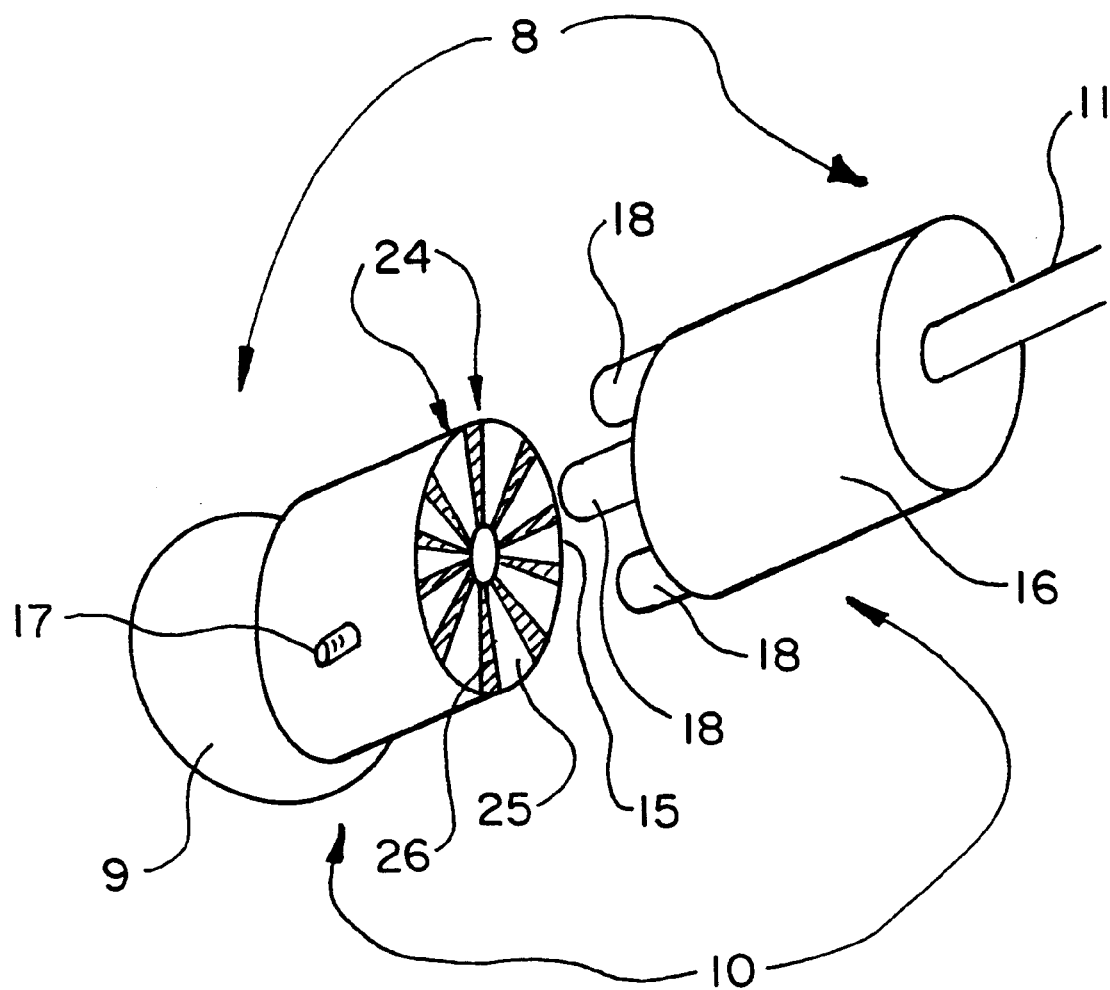
FIG. 2 is an exploded perspective view of ratchet components of the distractor illustrated in FIG. 1.

Ratchet 10 consists of the following components: geared face plate 15, pin house 16, attachment post 17 and engagement pins 18, springs 19, shape-memory-effect alloy wire 20, bias spring 21, adjustment screw 38, threaded adjustment hole 40, attachment lead 39, support pin 41, and support arm 22. Ratchet components are shown in FIG. 2. Face plate 15 is composed of a succession of wedges and radial teeth 24.

Ratchet 10 operates as follows. When shape-memory-effect alloy wire 20 is heated to its transition temperature, it forcefully shrinks in length. Heating is accomplished by Joule heating, that is, application of an appropriate electric current to the shape-memory-effect wire 20 that raises its temperature to at least its transition temperature. As shape-memory-effect alloy wire 20 is anchored to support arm 22 by screws 23, shortening causes gear face plate 15 to rotate in the direction of shrinkage. At least one of pins 18 whose length beyond pin house 16 is set by its spring 19 will engage at least one of radial teeth 26 so as to turn pin house 16 in the direction of wire 20 shrinkage.

Figure 4A:
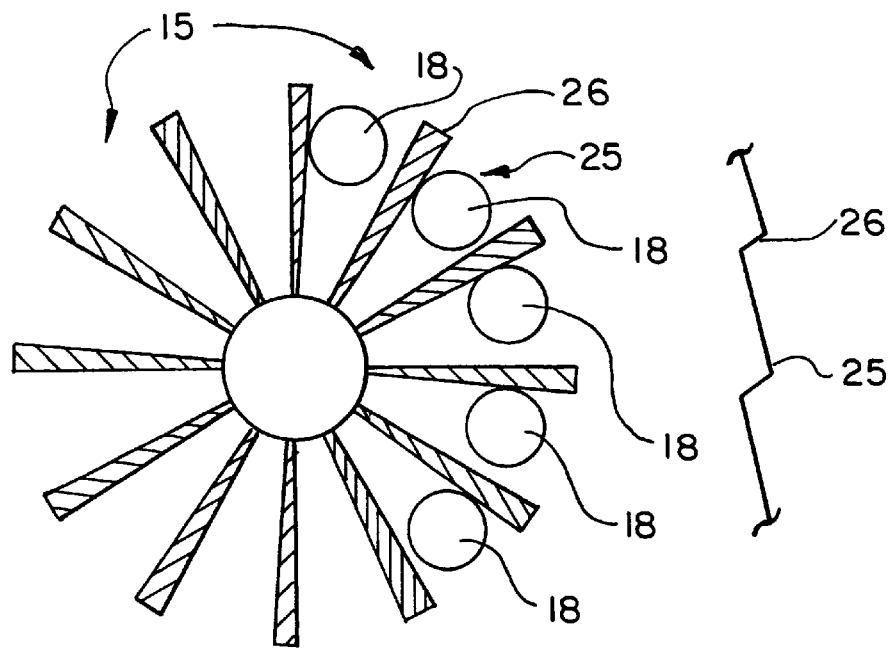
FIGS. 4A and 4B schematically illustrate a pin ratchet engagement of the distractor illustrated in FIG. 1 which produces finer rotational resolution.
Figure 4B:
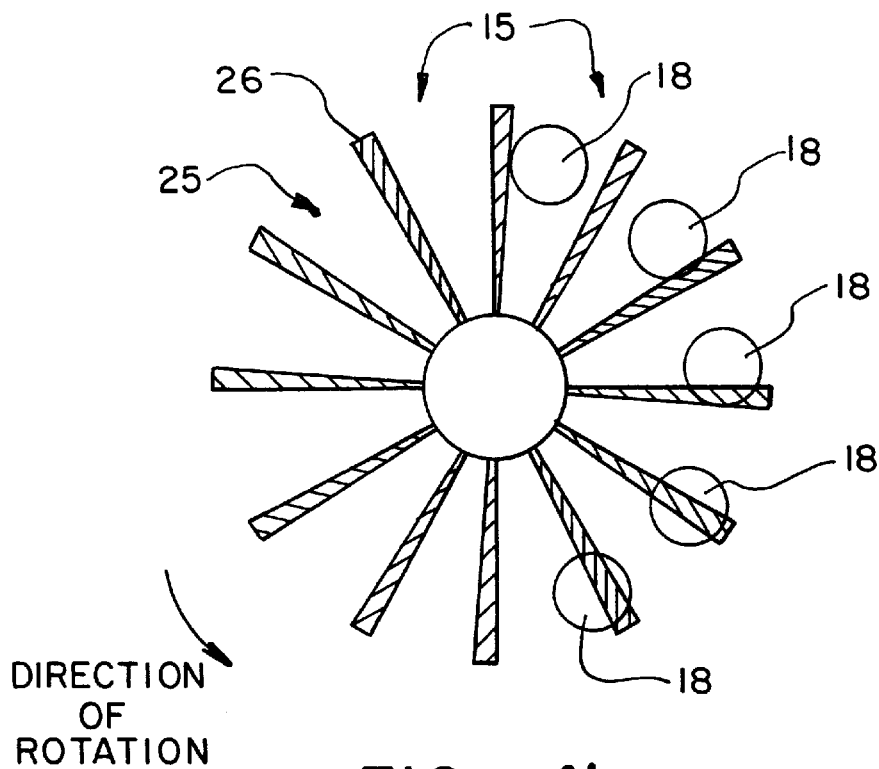

More specifically, the ratchet 10 is designed as follows. The number of radial teeth 26 on the gear face plate 15 resolves 360° of rotation into smaller angular segments. For instance, if the gear face plate 15 has 12 radial teeth 26, 360° is divided into segments of 300 (i.e., 360°/12). Conventionally in gear face plate arrangements the engaging pins 18 are spaced equal to the spacing of the teeth 26 as shown in FIG. 4A, such that all of the pins 18 simultaneously engage a respective tooth 26. The arrangement of the pins 18 extending from pin house 16 can be used to provide finer resolution as shown in FIG. 4c, thus reducing the rotation needed to advance the ratchet 10 so that it cannot slip back to it original position. For instance, if there is one pin 18 or m pins 18 spaced at 300 angular increments from neighboring pins 18, the ratchet 10 cannot resolve advancement into increments smaller than 30°. That is, the pin house 16 must rotate at least 30° to engage the pins 18 with radial teeth 12 so that it will not slip, as shown in FIG. 4.A. However, if the pins 18 are properly offset from 30° angular separation, the angular rotation required to advance the ratchet 10 is smaller. As an example, assume that there are five pins 18, designated "a" through "e". Consider FIG. 4B. Assume the gear face plate 15 is oriented such that one of the radial teeth 26 is vertical (at 12 o'clock on the face of a clock); thus each of the remaining eleven radial teeth 26 would be positioned at a numeral on the clock face, each 30° from its two neighboring numerals. Thus the radial teeth 26 are at 0°, 30°, 60° . . . 300° and 330°. Now align the pin house 16 so that "a" of pins 18 is at 12 o'clock. The five pins 18 can resolve rotational advancement down to 6° (30°/5) if positioned as follows: "a" at 0°, "b" at 36°, "c" at 72°, "d" at 108°, and "e" at 144°. Basically, the pins 18, as shown in FIG. 4B, are each positioned differently between two adjacent radial teeth 26 so that only 6° of rotation is needed for one of pins 18 to engage one of radial teeth 26. This concept is not limited to the example provided herein. It has the advantage that it produces fine ratcheting increments, but reduces the manufacturing difficulty and precision required to manufacture gear face plate 15 for such finer ratcheting increments. Again, referring to the example of 6° resolution, a gear face plate 15 with 60 radial teeth 26 would be required if the offset technique is not used.

As wire 20 cools, bias spring 21, attached to adjustment screw 38 and to attachment post 17 by attachment lead 39 which passes around support pin 41, stretches SME alloy wire 20 and also rotates gear face plate 15 opposite to that resulting from shrinkage of SME alloy wire 20 so that pins 18 slide over wedges 25 to a reset position without rotating screw 11. Adjustment screw 38 mates with threaded adjustment hole 40. Depending on the direction it is rotated, it alters the amount bias spring 21 is stretched, varying the bias force experienced by SME alloy wire 20.

Figure 12:
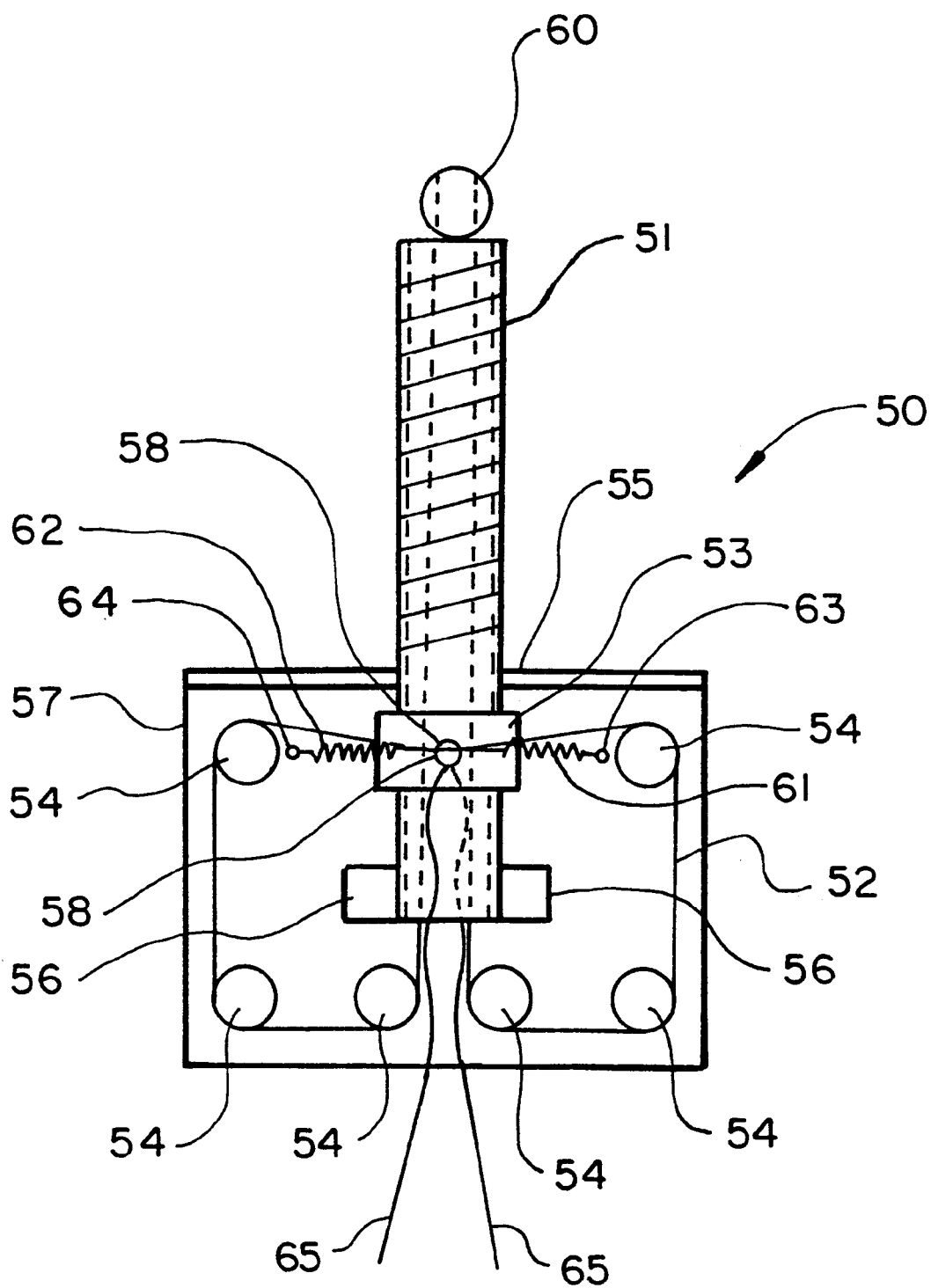
FIG. 12 is a schematic sectional view of an in-line electromechanical screw mechanism incorporating a ratchet device, with Nitinol wire positioned in a hollow in the center of the length of the partially threaded shaft that forms the basis of an implantable distractor according to another embodiment of the present invention.

It is an object of implantable embodiments of the present invention to eliminate the support arm 22 of the distractor 1 shown in FIG. 1 so that the SME alloy wire 20 and the bias spring 21 are aligned with the screw 11. Such an "in line" embodiment, because of its compact design, facilitates implantation. Such an improvement to distractor 1 is conceptually shown in FIG. 12. Note that support arm 22 has been eliminated and the SME alloy wire 20 in FIG. 1 is now enclosed. Instead of a complete Distractor (which would include mounting brackets), FIG. 12 shows the drive mechanism for the distractor, an electromechanical screw 50. It is composed of a hollow partially threaded shaft 51, an SME alloy wire 52, a ratchet 53, six guide pulleys 54, a bearing 55, a bearing 56, bias spring 61, bias spring 62, and a housing 57.

The SME alloy wire 52 attaches to diametrically opposite points on the ratchet 53; attachment can be made to small posts 58 as represented using crimps 59. These can also attach wires 65 used to connect electrical power to the SME alloy wire 52. An alternative means to connect the SME alloy wire 52 to the SME alloy wire 52 is with screw down terminals (not shown); these can also connect SME alloy wire 52 to wires 65. Also, attached to small posts 58 are both one end of bias spring 61 and one end of bias spring 62. The other end of bias spring 61 is attached to housing 57 by some method at connection 63. Similarly, the other end of bias spring 62 is attached to housing 57 by some method at connection 64. SME alloy wire 52 can be a continuous length of wire or two wires joined by barrel crimp 60. It is placed within the housing 57 and the hollow 61 of the partially threaded screw 51 along the longitudinal length of the distractor. This is preferred as sharply bending SME alloy wire 52 significantly weakens it at the bend point. Note it is assumed, but not shown, that small posts 58 are insulated from the ratchet 53.

The guide pulleys 54 are used to alter the positional direction of the SME alloy wire 52. When electrical current is supplied to wires 52, it contracts or shortens rotating ratchet 53, which in turn rotates partially threaded screw 51 causing bias spring 61 and bias spring 62 to both lengthen to increase the tangential reset force that ratchet 63 experiences. When electrical current is turned off, the SME alloy wire 52 cools so that bias spring 61 and bias spring 62 are able to reset the ratchet 53 and stretch SME alloy wire 52 to its original length without rotating partially threaded screw 51.

An in-line embodiment can be accomplished in an actuator mechanism that translates linear motion developed by an SME actuator into rotational motion that is then imparted to a screw. Several such motion translation mechanisms are possible. One incorporates a cylindrical cam and a ratchet where the ratchet controls the rotational freedom of the cylindrical cam. The same operation can be accomplished with a cylindrical cam and a roller clutch that controls the rotational freedom of the cylindrical cam.

For descriptiveness, the in-line designs will be termed as electromechanical screw mechanisms such as is shown in FIGS. 5A and B. The electromechanical screw 101 produces precise quantified rotation with high torque. The electromechanical screw 101 is composed of the following components: a partially threaded shaft 102; a bearing surface 103; a cylindrical cam 104; ratchet gear 105 with a first pawl 106 and a second pawl 107 set at different angles to ratchet gear 105 so that they alternately engage the ratchet gear 105; a Nitinol wire 108; a reset spring 109 and a ratchet enclosure 110. The ratchet gear 105 and cylindrical cam 104 are incorporated in one unit, cylindrical cam-ratchet gear unit 130.

Figure 6B:
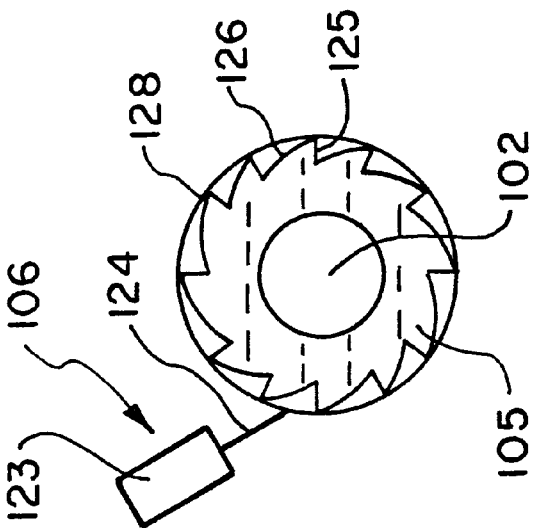
FIGS. 6A and B depict operation of a cylindrical cam-gear ratchet unit imparting one way motion to the distractor screw illustrated in FIG. 5A.
Figure 6A:
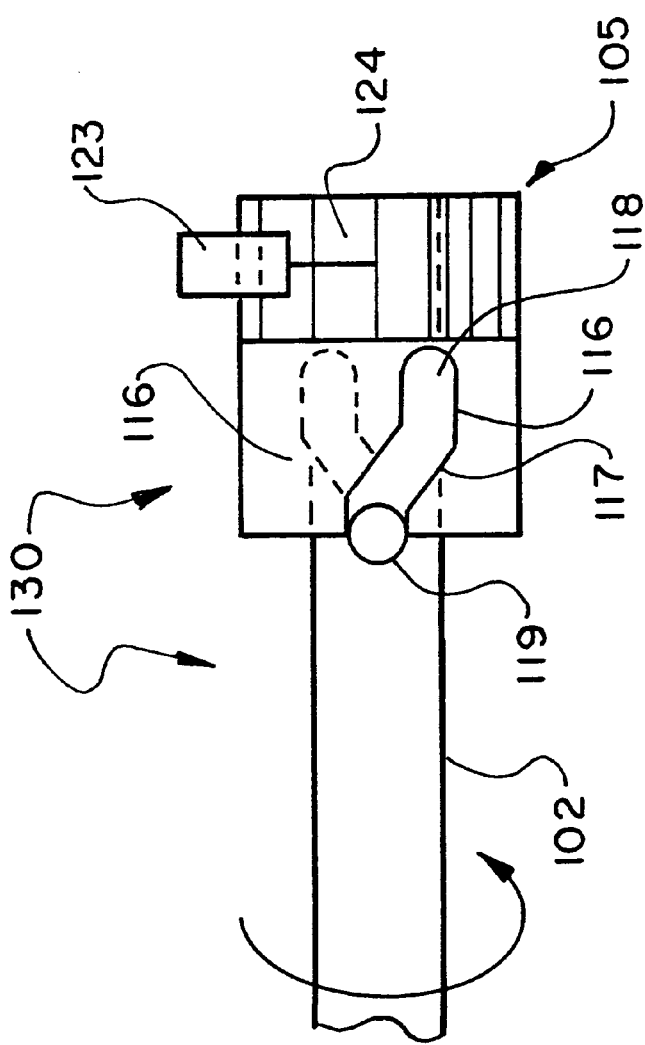

The principle for conversion of linear motion to rotational motion is shown in FIGS. 6A and B. FIGS. 6A and B show the cylindrical cam-ratchet gear unit 130 mounted on the partially threaded shaft 102 and one of the two pawls, specificity the first pawl 106. The ratchet gear 105 is shown with 12 teeth 128. The cylindrical cam 104 is formed by slots 116 cut on a spiral along the length of the cylindrical cam-ratchet gear unit 130. Slots 116 each consist of a first spiral section 117 and a second straight section 118. The first pawl 106 is locked in position relative to the ratchet gear 105 by its mounting in the housing. The first pawl 106 is shown engaging a flat edge 125 of teeth 129 of ratchet gear 105; the ratchet gear 105 can rotate only in a direction that causes flat edge 125 to move away from first pawl 106. The openings 131 of slots 116 are diametrically opposite each other and engage posts 119, mounted on partially threaded shaft 102 and perpendicular to its length. If cylindrical cam-ratchet gear unit 130 is angularly fixed and pulled toward posts 119, first spiral section 117 of slots 116 engages posts 119 to force partially threaded shaft 102 to rotate.

Figure 7A:
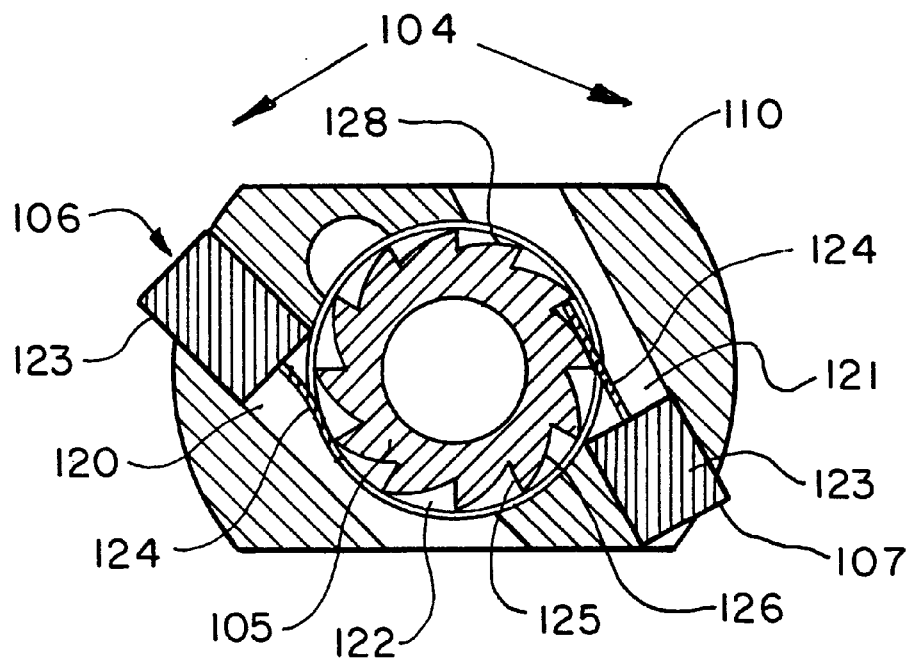
FIGS. 7A and B are cross-sectional views of the ratchet gear of the screw mechanism illustrated in FIG. 5A showing the positioning of pawls of the ratchet.
Figure 7B:
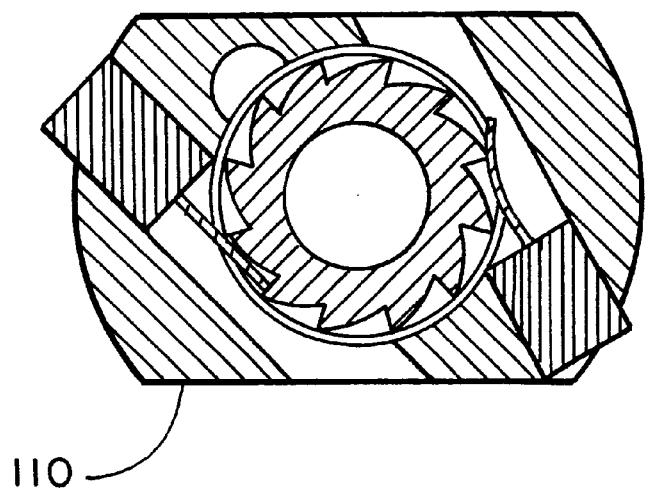

FIGS. 7A and B clarify the ratcheting process. The ratcheting consists of the ratchet gear 105, a first pawl 106 and a second pawl 107 that are friction fit into a first pawl cavity 120 and a second pawl cavity 121, respectively, 1 within the ratchet enclosure 110. The ratchet gear 105 resides in a cylindrical cavity 122 within the ratchet enclosure 110. The first pawl 106 and the second pawl 107 each consist of a flexible spline 124 attached to a plug 123. The plug 123 of the first pawl 106 and the second pawl 107 are retained by friction within a first pawl cavity 120 and a second pawl cavity 121, respectively. The flexible spline 124 engages the teeth 128 of the ratchet gear 105. The teeth 128 each have a flat edge 125 and a curved edge 126. The flat edge 125 engages the flexible spline 124 to prevent the ratchet gear 105 from rotating backwards. The curved edge 126 flexes the spline out and away from the ratchet gear 105 as it rotates in the advancing direction. Note that flexible spline 124 of first pawl 106 and flexible spline 124 of second pawl 107 are positioned in ratchet enclosure 110 such that one engages flat edge 125 while the other is pushed away by curved edge 126. The engagement/disengagement alternate on each activation effectively doubling the incremental steps provided in the ratcheting unit per revolution.

The Nitinol wire 108, when electrically energized, acts as an electromechanical actuator to produce rotation of the partially threaded shaft 102. It does so by pulling the ratchet gear 105 along a smooth section 127 of the partially threaded shaft 102 against the reset spring 109. As the ratchet gear 105 is pulled, compressing the reset spring 109, first spiral section 117 of slots 116 of cylindrical cam 104 interact with posts 119 in and perpendicular to length of partially threaded shaft 102 to cause partially threaded shaft 102 to turn through a fixed angle. When the Nitinol wire 108 is de-energized, the reset spring 109 pushes the cylindrical cam-ratchet gear unit 130 back to its original linear position on the partially threaded shaft 102 and also stretches the Nitinol wire 108. As the cylindrical cam-ratchet gear unit 130 is reset, it also rotates so as to align the flat edge 125 of one of teeth 128 with the one of first pawl 106 or second pawl 107.

Figure 11:
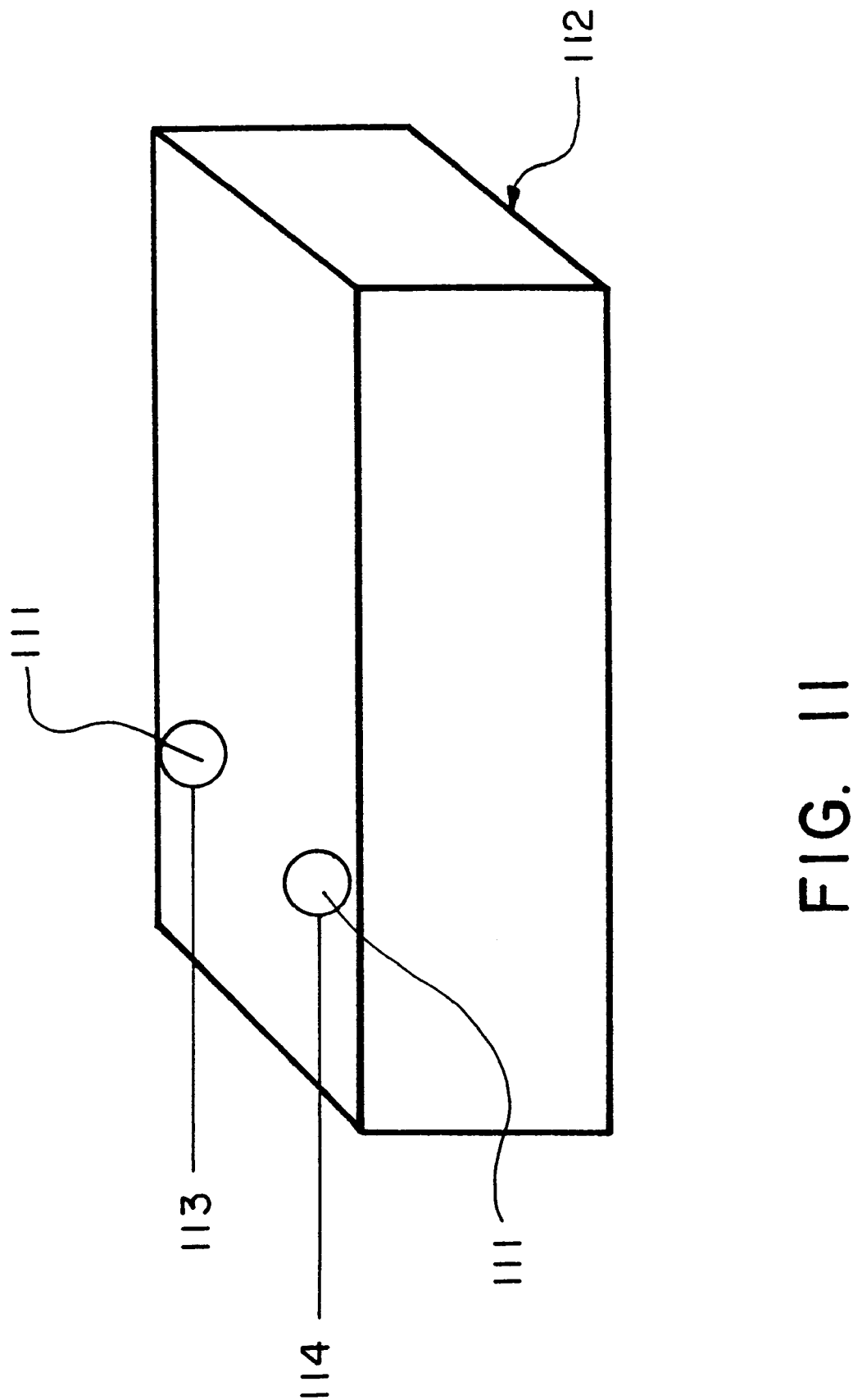
FIG. 11 is a view of a power supply connection for use with the implantable distractors of the present invention.

As shown in FIG. 11, the terminals 111 of an electrical current source 112 are attached to first crimp 113 and second crimp 114 by leads 129. The Nitinol wire 108 runs from first crimp 113 to third crimp 115 and back to second crimp 114 to complete the circuit. When current is applied, the temperature of the Nitinol wire 108 is elevated through Joule heating to its transition temperature, causing it to shorten forcefully. Cylindrical cam-ratchet gear unit 130 is pulled along partially threaded shaft 102 by the shortening of Nitinol wire 108 so that reset spring 109 is compressed. First spiral section 117 of slots 116 in cylindrical cam 104 mate with posts 119 on partially threaded shaft 102. If ratchet gear 105 is prevented from rotating, accomplished by either first pawl 106 or second pawl 107 engaging flat edge 125 of teeth 128 of ratchet gear 105, as first spiral section 117 is pulled along posts 119, the partially threaded shaft 102 is rotated through some angle. As second section 118 is pulled along posts 119, partially threaded shaft 102 does not rotate. Posts 119 and cylindrical cam 104 thus ensure that partially threaded shaft 102 is rotated through a precise angle, reducing requirements for precision in the amount of shortening of the Nitinol wire 108 component with Joule heating.

When current ceases, the Nitinol wire 108 cools below its transition temperature; the reset spring 109 is able to relax, linearly repositioning the cylindrical cam-ratchet gear unit 130 to its original location on the partially threaded shaft 102 (while it is incidentally rotated by the posts 119 and first spiral section 117 of slots 116 of cylindrical cam 104) and, simultaneously stretching the Nitinol wire 108 to its original length.

As part of an implanted or buried distractor, the electromechanical screw 101 is mounted into brackets (not shown) attached to the bone on each side of an osteotomy.

Figure 8:
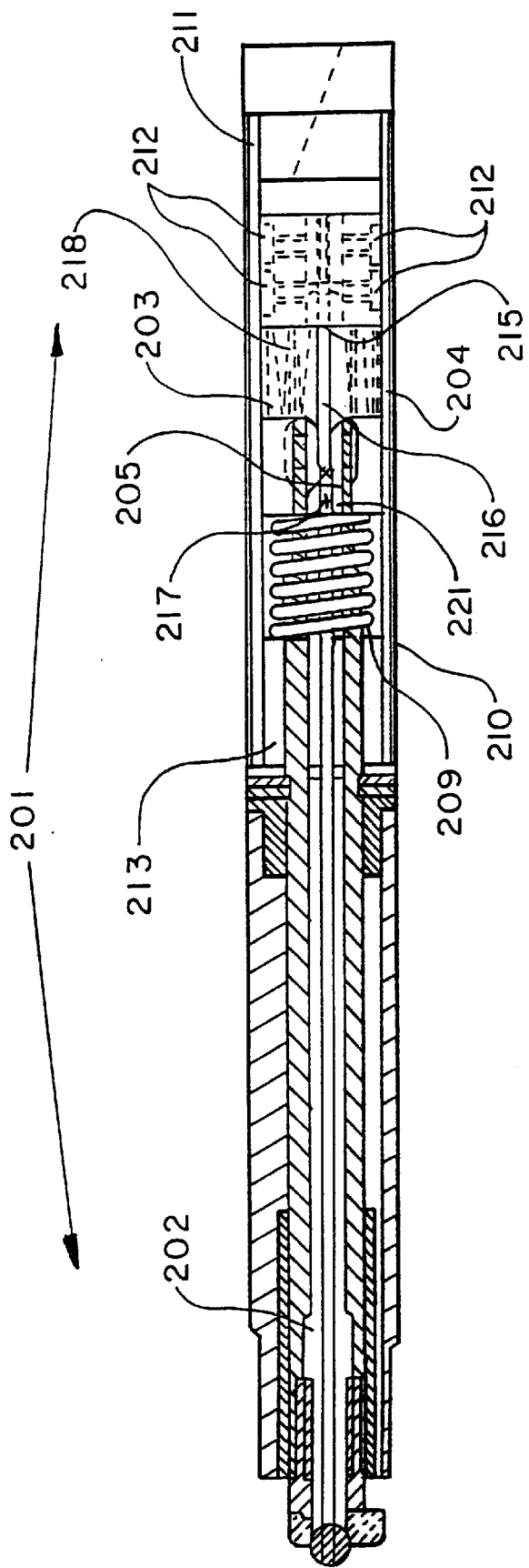
FIG. 8 is a sectional view of an in-line electromechanical screw mechanism incorporating a cylindrical cam-pin ratchet, with Nitinol wire positioned in a hollow in the center of and the length of the partially threaded shaft that forms the basis of an implantable Distractor according to another embodiment of the present invention.

FIG. 8 shows a another embodiment of the electromechanical screw mechanism 201 that can be used in an implantable distractor. This embodiment is more robust and offers finer ratcheting increments. It incorporates a ratchet 204 similar to the embodiment in the "proof-of-concept" distractor 1 shown in FIG. 1 and a cylindrical cam 205, incorporated into the cylindrical cam-pin house unit 203. The cylindrical cam 205 engages and rotates the partially threaded shaft 202 similar to electromechanical screw 101; the ratchet 204 ensures one way incrementation.

The electromechanical screw 201, as shown in FIG. 8, is composed of six major components: a partially threaded shaft 202; a bearing surface 213; a ratchet 204 gear face plate 215 composed of a succession of wedges and radial teeth 224; pin house 216 with engagement pins 218 and springs 219; a Nitinol wire 208; a reset spring 209 and a ratchet enclosure 210. The cylindrical cam-pin house unit 203 is mounted on the partially threaded shaft 202; it can both slide and rotate on the partially threaded shaft 202. Gear face plate 215 is free to slide in ratchet enclosure 210 but cannot rotate due to engagement of enclosure slot 211 cut in enclosure 210 and locking pins 212 mounted in gear face plate 215.

The Nitinol wire 208, when electrically energized, acts as an electromechanical actuator to produce rotation of the partially threaded shaft 202. It does so by shortening and consequently pulling the gear face plate 215 within ratchet enclosure 210 and cylindrical cam-pin house 203 along the partially threaded shaft 202 against the reset spring 209. As the cylindrical cam-pin house unit 203 and gear face plate 215 are pulled, compressing the reset spring 209, first spiral section 221 of slots 217 cut in cylindrical cam 205 at an angle to the length of the partially threaded shaft 202 interact with posts 220 mounted in and perpendicular to length of partially threaded shaft 202 to cause partially threaded shaft 202 to turn through a fixed angle. When the Nitinol wire 208 is de-energized, the reset spring 209 pushes the cylindrical cam-pin house unit 203 back to its original position on the partially threaded shaft 202 and gear face plate 215 to its original position in the ratchet enclosure 210; and it also stretches the Nitinol wire 208. Note that gear face plate 215 continuously engages engagement pins 218 of pin house 216; springs 219 ensure that this occurs properly. Gear face plate 215 cannot rotate relative to ratchet enclosure 210. Thus when Nitinol wire 208 shortens, cylindrical cam-pin house 203 cannot rotate when first spiral section 221 of slots 217 engage posts 220, thus imparting rotation to the partially threaded shaft 202. However, as the Nitinol wire 208 relaxes and reset spring 209 returns cylindrical cam-pin house unit 203 and gear face plate 215 to their reset position, cylindrical cam-pin house unit 203 is able to and does rotate without affecting orientation of partially threaded shaft 202. The resolution of the ratchet 204 is again established as shown in FIG. 4.

Figure 9:
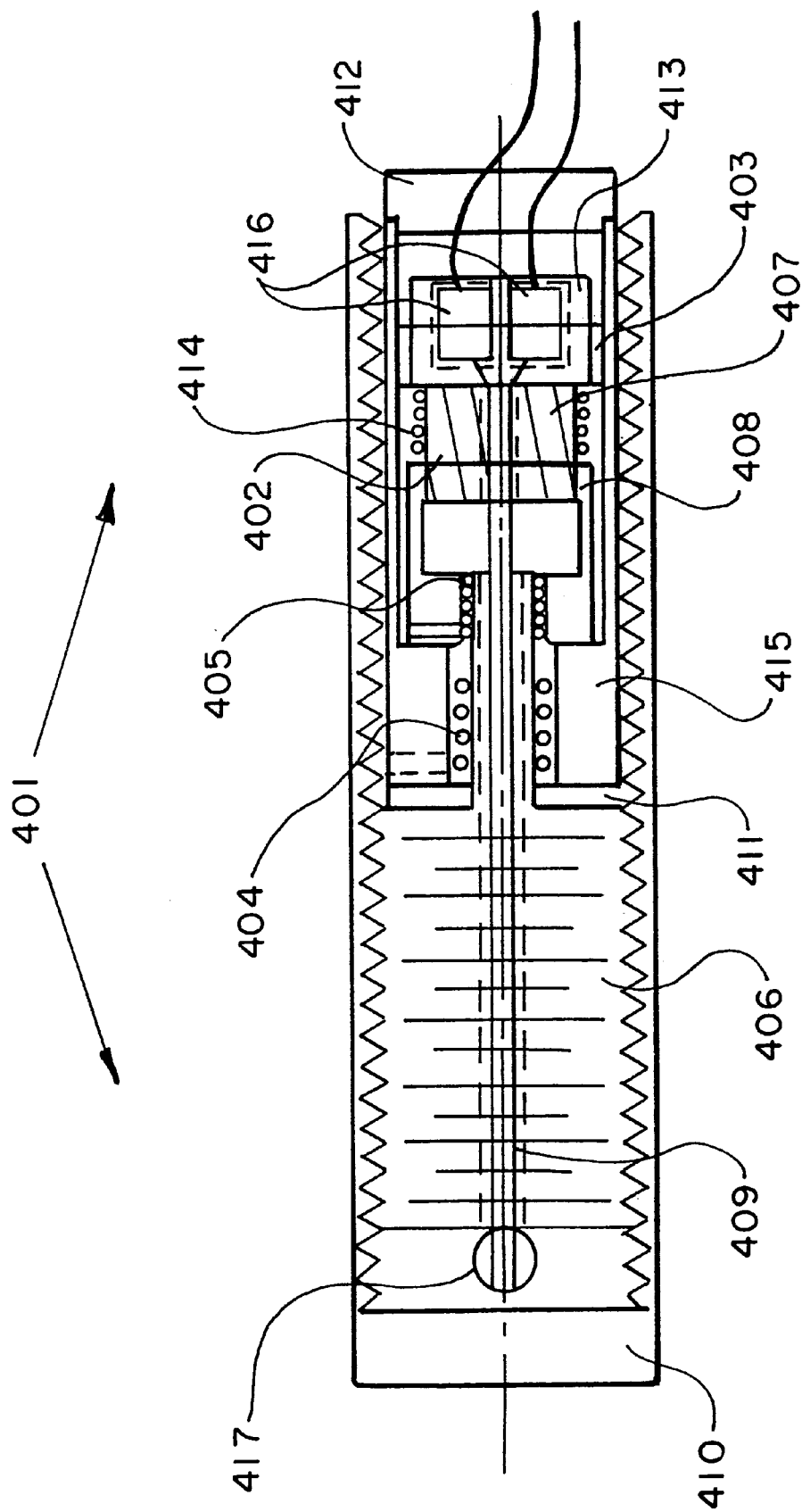
FIG. 9 is a sectional view of an in-line electromechanical screw mechanism incorporating a spiral drive and wrap spring clutch, that forms the basis of an implantable Distractor according to another embodiment of the present invention.

FIG. 9 also depicts another embodiment of an electromechanical screw mechanism 401 that can be used in a distractor. This embodiment is simpler, more robust and offers finer ratcheting increments. It comprises a spiral rod segment 402 and guide 403, a first wrapped spring clutch 404, a second wrapped spring clutch 405, a partially threaded shaft 406, a helix drive 407, a helix sleeve 408, a Nitinol actuator wire 409, threaded sleeve 410, a first washer 411, an end cap 412, a crimp housing 413, a bias spring 414 and a motor housing 415.

Figure 13:
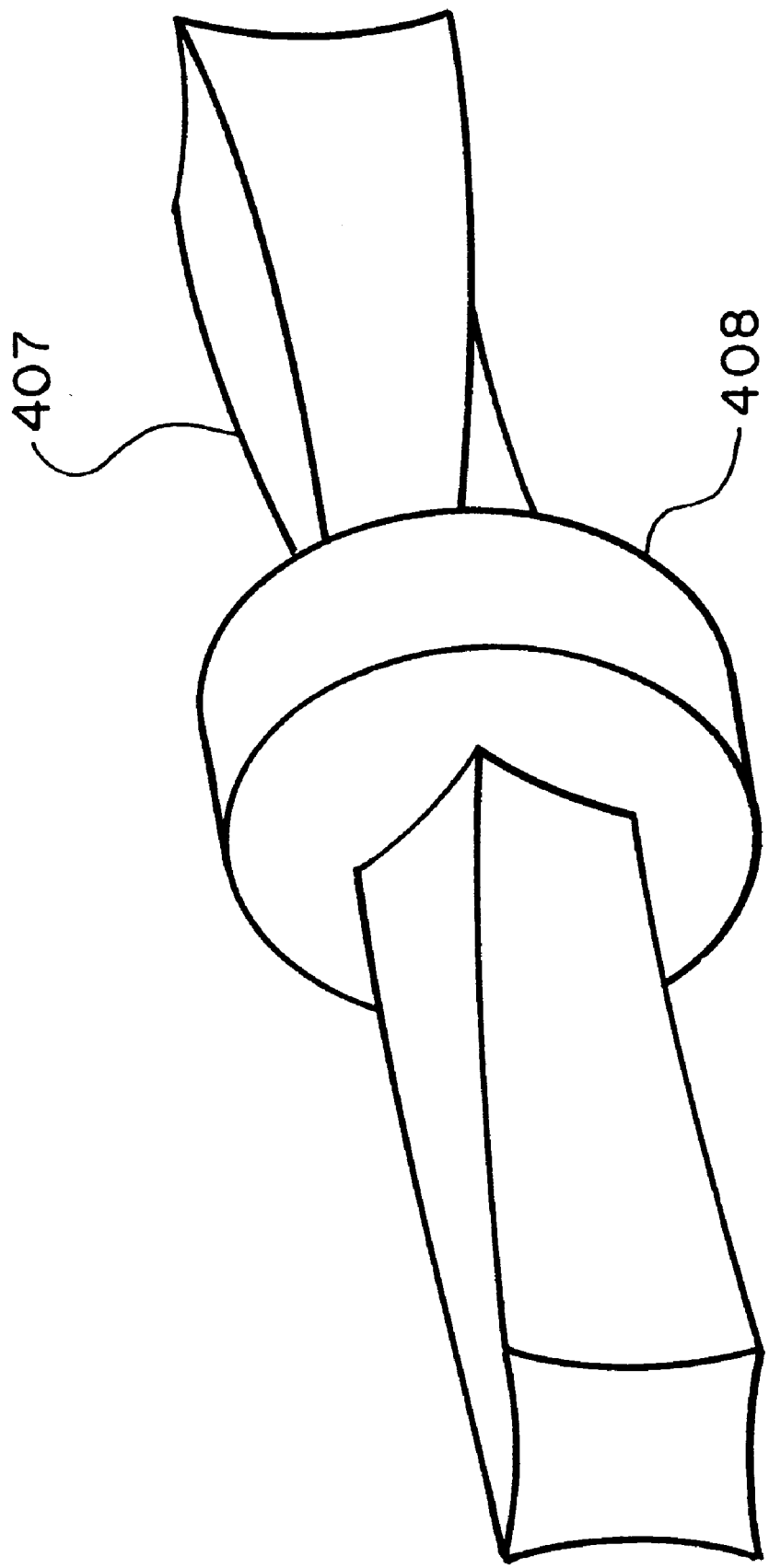
FIG. 13 is a perspective view of a spiral drive for use with a distractor according to the present invention.

Again, the electromechanical screw 401 operates through joule heating of the Nitinol actuator wire 409. The Nitinol actuator wire 409 is anchored between the crimp housing 413 and the distal end of partially threaded shaft 406 by crimps 416 and barrel crimp 417. The barrel crimp 417 is used to joint two pieces of Nitinol wire rather than merely providing a support over which a single wire is looped. Looping creates a point of high stress which can lead to breakage. Bias spring 414 is a compression spring that maintains a bias tension on the Nitinol actuator wire 409. The internal mechanism translates linear motion from the shortening of the Nitinol actuator wire 409 to rotational motion via the helix drive 407 and helix sleeve 408. The mechanism is represented in FIG. 13. It can be seen that, with the helix drive 407 fixed, the helix sleeve 408 rotates as helix drive 407 is longitudinally pushed through the helix sleeve 408. Initially, the second wrapped spring clutch 405 is engaging partially threaded shaft 406. The first wrapped spring clutch 404 is not engaging partially threaded shaft 406. When the Nitinol actuator wire 409 is heated, it shortens. It forcefully pulls the crimp housing 413 toward the washer 411, crimps 416 engaging the crimp housing 413. The helix drive 407 is forced through the helix sleeve 408 so that it rotates. The second wrapped spring clutch 405 engages the partially threaded shaft 406, imparting rotation generated by the helix drive 407 being pushed through helix sleeve 408, to the partially threaded shaft 406. In the process, bias spring 414 is further compressed. As the Nitinol actuator wire 409 cools, it relaxes and is stretched to its original length by the decompressing bias spring 414. The second wrapped spring clutch 405 disengages from the partially threaded shaft 406. Simultaneously, the first wrapped spring clutch 404 engages to prevent reverse rotation of the partially threaded shaft 406.

Figure 14:
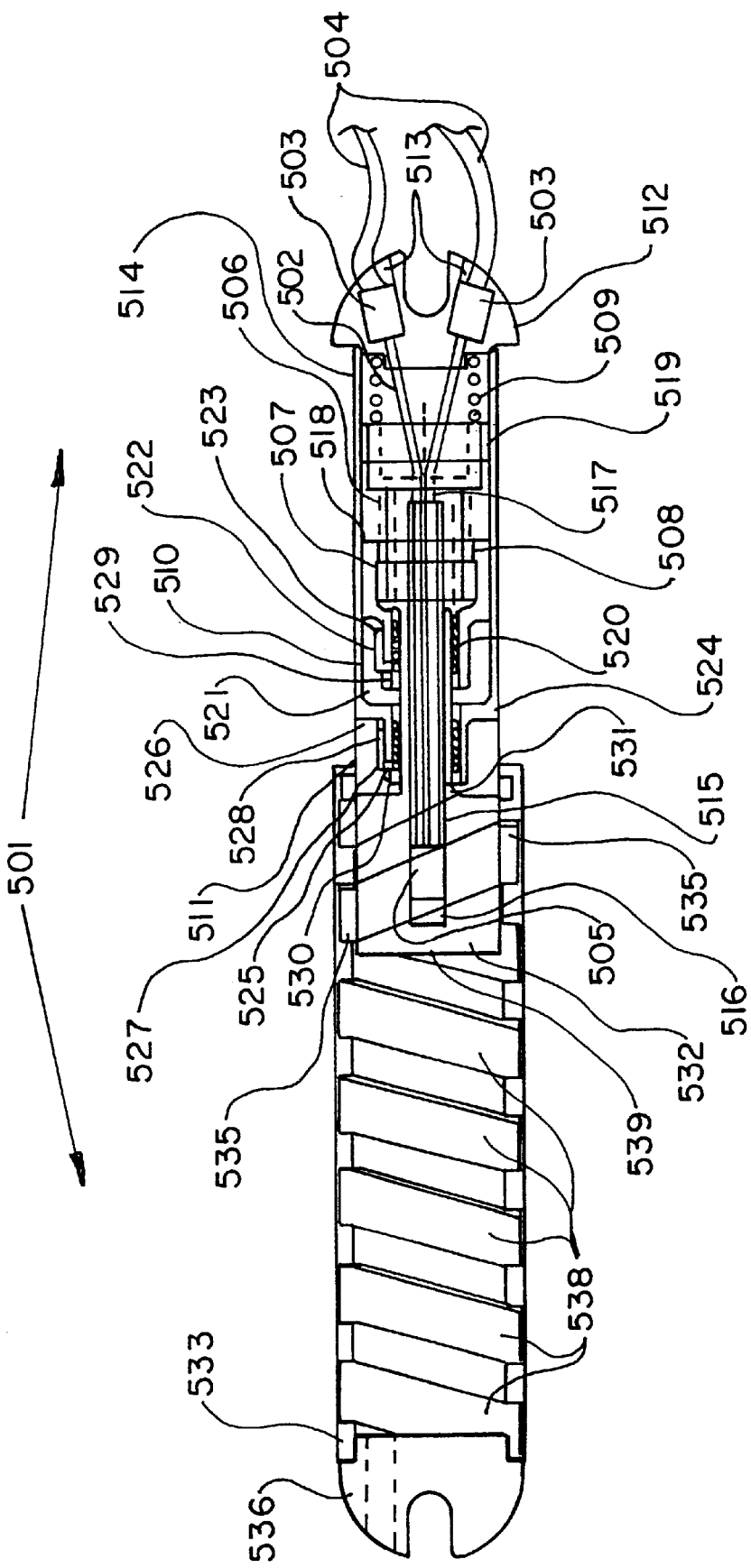
FIGS. 14 A and B schematically illustrates a distractor according to another embodiment of the present invention.

Internal friction in all of the above embodiments significantly reduces the efficiency of the device. This is an inherent problem with screw mechanisms. Also, the above described devices seek to cause relatively rapid bone movements against the elasticity of soft tissue, although these movements are limited to extremely small increments of about 0.1 mm or less. The distractor 501 shown in FIGS. 14A and B is designed to reduce both of these concerns. With regard to reducing screw friction, the standard screw is replaced with either a ball screw or a roller screw. Here, a roller screw is shown. The sliding action of thread on thread is replaced with a rolling device positioned in a special thread. Typically, such devices are designed for extended use and are operated at high speed with lubrication. The distractor 501 application involves only very short periods of use at relatively low speeds. Lubrication is not an option due to biocompatability issues and lack of effectiveness at low speed. The force to generate motion provides that a Nitinol actuator is electrically actuated to compress a drive spring to store energy. When the electrical current is turned off, the spring tries to return to its original length. In returning to its original length the spring pushes a spiral shaft through a mating nut to convert linear motion to rotational motion. The shaft is linked to the low friction screw by a clutch system, in particular, two wrapped spring clutches, to cause the low friction screw to rotate only in one direction. As in the previous embodiments, this one way rotation is used to expand an osteotomy site. Referring to FIGS. 14A and B electric current is supplied to the electrical conductors 504. Crimps 503 mechanically and electrically join electrical conductors 504 to Nitinol wire 502. Crimps 503 rest in slots 513 in first end piece 512 which is locked into an end of cylindrical wall 514. Crimp 505 mechanically reinforces the Nitinol wire 502 to ensure it is electrically continuous and locks it within rigid sleeve 515. Rigid sleeve 515 resides within lumen of the roller bearing screw 516 and lumen of spiral shaft 517 to join them and maintain separation therebetween. Storage spring 509 maintains a bias tension in Nitinol wire 502 by applying an expansive force between spiral rod 506 and end piece 512.

Spiral rod 506 is free to move parallel to the length of cylindrical wall 514 but is rotationally fixed by nut or sleeve 519. Spiral rod 519 passes through spiral guide hole 508 in washer 507. Washer 507 is fixed to support 518 which is free to rotate.

First wrap spring clutch 510 consists of support 518, spring 520 and lock ring 521. Tab 523 of spring 520 extends through slot 529 in support 518. Slot 522 in lock ring 521 engages tab 523 of spring 520 to stabilize tab 523 of spring 520 preventing rotation of spring 520 relative to support 518.

The second wrap spring clutch 511, similar to the first wrap spring clutch 510, consists of support 524, spring 525 and lock ring 526. Tab 528 of spring 525 extends through slot 530 in support 524. Slot 527 in lock ring 526 engages tab 528 of spring 525 to stabilize tab 528 of spring 525 preventing rotation of spring 525 relative to support 524.

Consider the distractor 501 when the storage spring 509 is at its maximum allowed extension. When electric current is applied to distractor 501, Nitinol wire 502 forcefully shortens. Crimp 505 pulls against rigid sleeve 515. Rigid sleeve 515 slides within lumen 516 and lumen 517 toward first end piece 512, pushing spiral rod 506 against storage spring 509 to compress it against first end piece 512. Second wrap spring clutch 511 prevents rotation in shaft 531 that would cause screw cover 533 to be drawn toward first end piece 512. More simply, the spring 528 engages the shaft 531. When electric current is removed from distractor 501, Nitinol wire 502 relaxes as heat is radiates away from it. Storage spring 509 expands to apply a pushing force against spiral rod 506 so that it slides away from the first end piece 512. Spiral rod 506 engages spiral hole 508 causing washer 507 to rotate. As washer 507 is fixed to support 518 of first wrap spring clutch 510, support 518 and lock ring 521 rotate in the same direction. Spring 520 tightens around shaft 531 of roller bearing screw 532 causing it to turn. As first wrap spring clutch 510 engages shaft 531 and rotates it, second wrap spring clutch 511 disengages from shaft 531 due to its direction of rotation.

The screw mechanism rotated by the arrangement in FIGS. 14A and B can be any of numerous low friction screws generally known in the art. Roller screw 534 is shown in FIGS. 14A and B. Shaft 531 of roller screw 534 engages both first wrap spring clutch 510 and second wrap spring clutch 511. Head 539 of roller screw 534 mates with screw cover 533. Rollers 535 are rotationally mounted in the head 539 with pins 537. Rollers 535 roll against square threads 538 in screw cover 533. As described above, roller screw 534 can only rotate in the direction which causes screw cover 533 to move away from first end piece 512.

Figure 15:
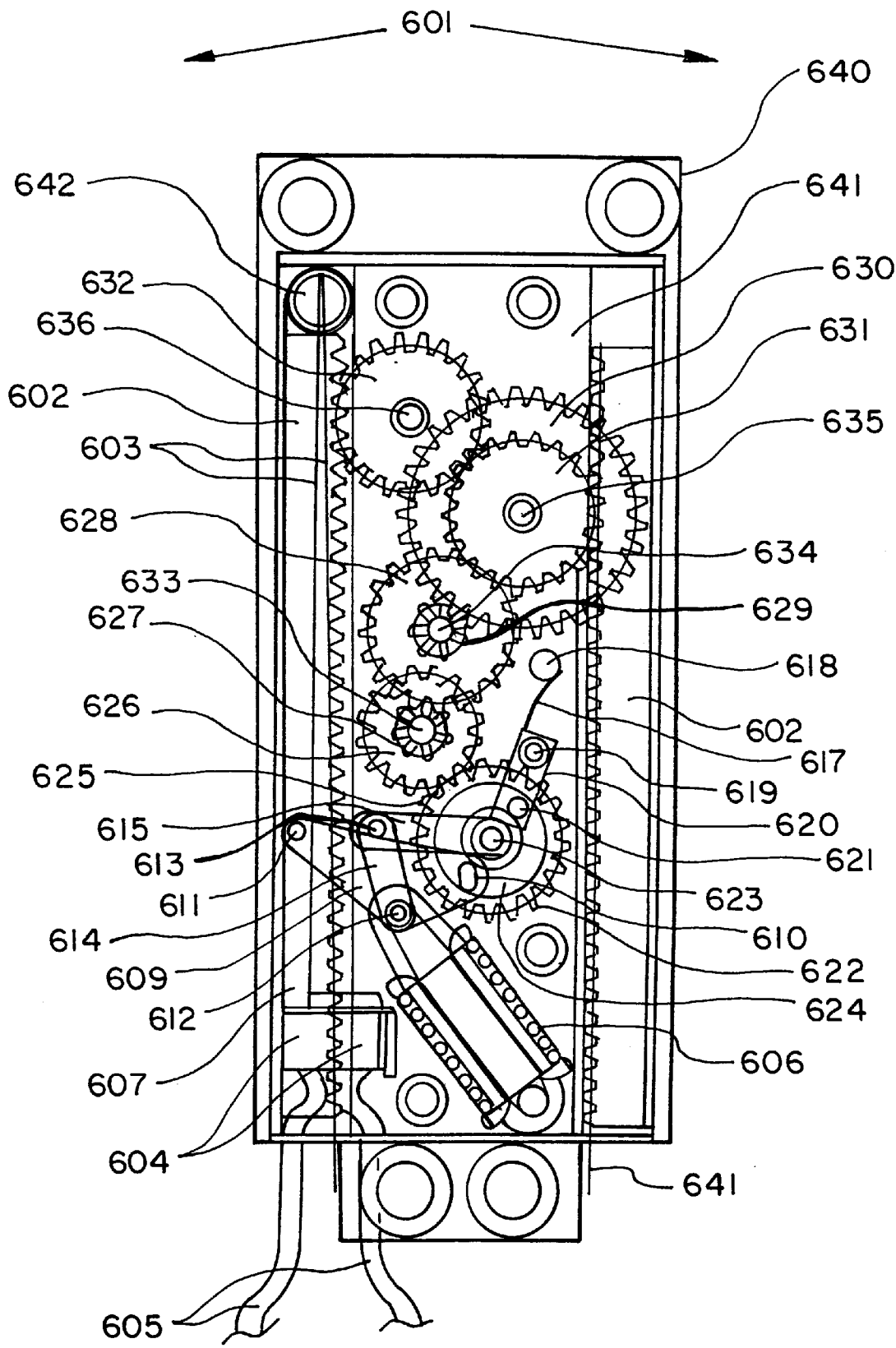
FIG. 15 schematically illustrates an implantable distractor according to another embodiment of the present invention.

A final embodiment is illustrated in FIG. 15 and utilizes low friction rack and gear technology as part of the motor for the distractor. The motor includes a ratchet mechanism which is driven by applying an electric current to Nitinol wire to produce self heating. The ratchet drives a gear train which engages a rack. As the gears of the gear train rotate, the rack advances to produce an increase in length of the unit.

The distractor 601 is shown in FIG. 15 and includes a cover 640 and base 641. Racks 602 are fixed to the cover 640. Base 641 slidably engages cover 640. Incremental lengthening occurs when an electrical current pulse is applied to the Nitinol wire 603 through conducting wires 605. The electric current elevates the temperature of the Nitinol wire 603, causing it to shorten. Slide 607 is pulled toward wire fixation terminal 642 made of an insulation material and attached to the base 641. This linear movement engages ratchet 608 which includes fixed arm 609, engagement wedge 610, pivot 612, pivot 613, second arm 614, third arm 615, ratchet wheel 622, axle 623 and brake 616. Brake 616 includes pivot 619, brake arm 620, and brake wedge 621 fixed to the brake arm 620. The first arm 609 moves with slide 607 at its pivot 611 and also rotates. Engagement wedge 610 engages slot 624 in ratchet wheel 622, ratchet wheel 622 rotates thereby rotating gear 625 attached to it. Gear 625 is the first gear of the gear train which includes gears 625, 626, 627, 628, 629, 631 and 632. Rotation of gear 625 will rotate these gears of the gear train appropriately. The clockwise rotation of gear 632 and the counterclockwise rotation of gear 631 slide base 641 out of cover 640 to lengthen the distractor 601.

When electrical current is discontinued, Nitinol wire 603 cools and begins to relax. Bias spring 606, which was stretched in the contraction of the Nitinol wire 603, now contracts stretching the Nitinol wire 603 and returning slide 607 to its starting position. Brake spring 617 engages post 618 to rotate brake arm 620 about pivot 619. Brake tab 621 applies force to ratchet wheel 622 and, through friction, prevents any reverse rotation of ratchet wheel 622. Engagement wedge 610 interacts with ratchet wheel 622 to lock the system at its new length.

Figure 10:
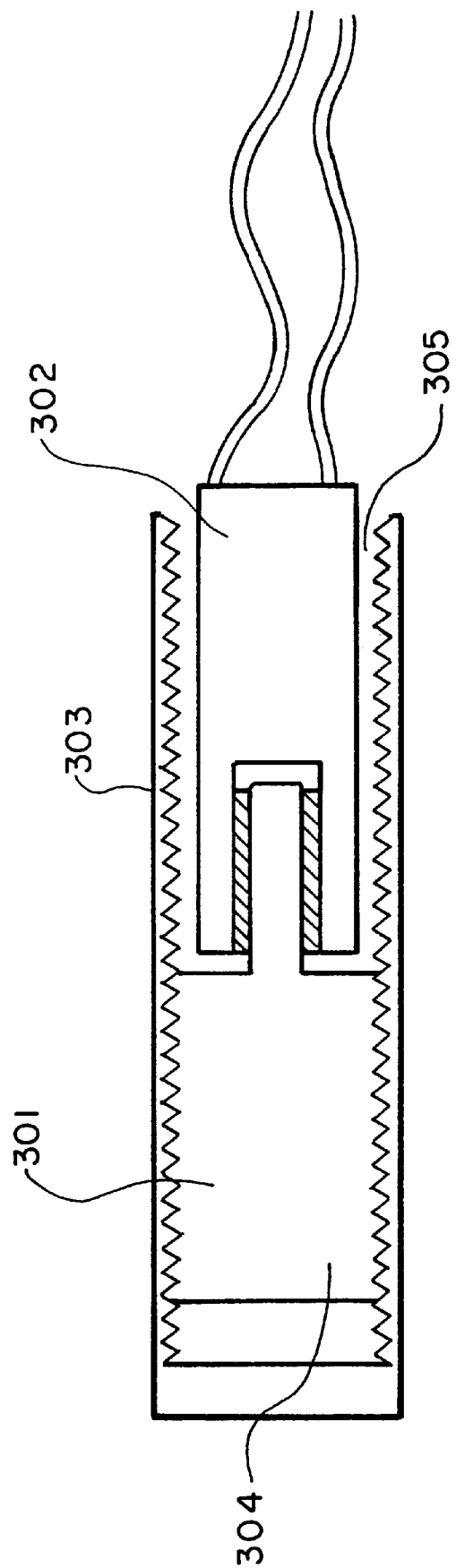
FIG. 10 is a view of a telescoping means for use with an electromechanical screw mechanism of the distractors of the present invention.

The initial implantation length of the distractor unit is often important due to the need to fit the device to a short bone segment. However, it is still important to have the capability to significantly augment a bone dimension such as length. This can be accomplished with the concept of telescoping. For example FIG. 10 shows the cross-section of an electromechanical screw and an outer concentric housing that can telescope over the ratchet housing and screw. Housing 302 contains the mechanical components to create rotational motion to turn screw 301. As screw 301 turns, threads 304 also are rotated. These engage threads 305 of shell 303, causing shell 303 to advance away from housing 302. Note that only housing 302 requires meticulous seals to prevent body fluids from entering and its internal volume is constant. Screw 301 and shell 303 do not require sealing. Also, if shell 301 and housing 302 were telescoped to created a combined internal space as the units slid apart, the internal volume expands, thus creating reduced pressure that would tend to suck fluid into the space, making sealing more difficult and also increasing the effective load against which the device must work.

There are various means to accomplish Joule heating of shape-memory-effect wire of the distractors:

1) an external electronic current supply connected percutaneously directly to the shape-memory-effect wire;
2) transmission of radio frequency (RF) energy to the Distractor that is accumulated and stored in a storage capacitor that, at an appropriate level, delivers the energy by means of an electric current to the shape-memory-effect wire; or
3) implantation of a battery of appropriate voltage with the Distractor; control circuitry opens and closes an electronic switch that connects the battery across the shape-memory-effect wire. FIG. 11 schematically illustrates an implantable power supply with appropriate electrical leads.

The details of electronic circuitry to implement operation as described briefly above are known to those skilled in the art.

Figure 16:
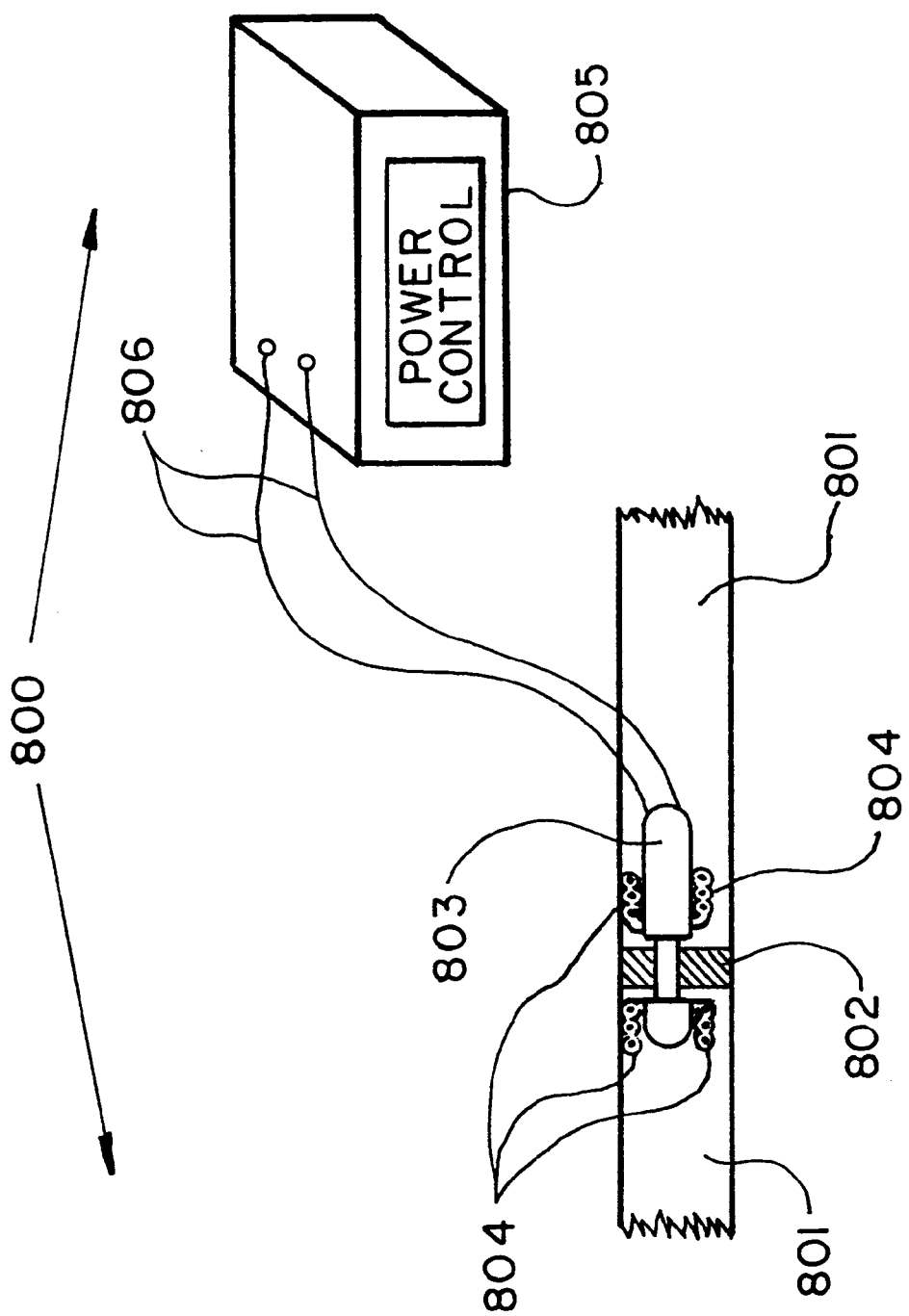
FIG. 16 schematically illustrates an implantable distractor according to any one of the disclosed embodiments with bilateral, multi-hole attachment plates and a microprocessor controller.

FIG. 16 schematically illustrates an implantable distractor 803 in a clinical installation, however, a distractor according to any one of the disclosed embodiments may be used. The distractor 803 is shown partially telescoping and attached to bone 801 across partially expanded osteotomy site 802 by bilateral multi-hole plates 804 affixed to distractor 803. Microprocessor-controlled power supply 805 is electrically connected to distractor 803 by insulated conductors 806. The bilateral multi-hole plates 804 are of a biocompatible metal or alloy such as titanium or stainless steel as is the distractor. Bilateral multi-hole plates 804 are shown configured as manufactured. The multi-hole plates 804 may be modified by appropriate bending and cutting to conform to the contour of the bone 801 at the attachment site. During surgery, the surgeon, with appropriate tools, has the option of removing any of the four bilateral multi-hole plates 804 or reducing the number of holes in any plate using an appropriate cutting and shaping tool. The multi-hole plates 803 may be attached to the bone 801 by screws. Distractor 803 is fixed to the bone surface by placing a screw through each hole, the head of the screw engaging bilateral multi-hole plates 804 as the screw is tightened into the underlying bone 801. In the above-described embodiments, the Nitinol wire is preferably positioned in a sealed chamber of constant volume, as shown above. The microprocessor controller may be integral or separate from the power supply 805, both of which may be external or may be implanted.

All of the above described implantable distractors eliminate the drawbacks of the known prior art distractors. All of the distractors use Nitinol wire to provide efficient, consistent dimensional changes for operation of the distractor. The length of Nitinol wire is generally run along the length of the distractor, generally along the direction of distraction, to provide sufficient length of Nitinol to have appropriate dimensional change to mechanically actuate the distractor. Additionally, due to the dimensional changes of the Nitinol wire only certain types of connections or attachments will effectively and consistently hold the Nitinol wire. Welding or soldering of the Nitinol wire tends to become loose and ineffective. The present invention utilizes crimping type connections or screw down type connections for the Nitinol wire. Additionally the connections for the Nitinol wire in many embodiments of the present invention serve as both an electrical connection and a mechanical connection. Specifically, the connections are used to both attach the Nitinol wire to electrical leads and to mechanically fix the Nitinol wire within the distractor.

All of the above described distractors allow for the method of bone distraction simulating natural bone growth according to the present invention. The method of the present invention essentially comprises the steps of: mounting an electrically powered automatic bone distractor across the portion of the bone to be distracted; dividing a daily distraction distance into a plurality of small incremental distances, each said incremental distance being less than about 0.1 mm; and automatically activating the distractor at distinct times for each incremental distance. As discussed above, preferably the electrically powered distractor is implanted. The distractor of the present invention can distract in increments less than 0.02 mm, specifically about 0.015 mm. Therefore, the method of the present invention may use increments of between 0.01 mm and 0.02 mm. It is contemplated that the individual distractions will be evenly spaced throughout the day, such as every 20 minutes. It is also possible to have all of one day's distractions occur over a specific, shorter time, such as corresponding to when the patient is asleep. Additionally, the activation is through a microprocessor controller. The microprocessor controller may be connected to said electrically powered distractor by electrical connections running from the microprocessor controller to the electrically powered distractor, or may utilize RF based activation.

The disclosed embodiments are intended to be illustrative of and not limiting to the present invention. It will be apparent to those of ordinary skill in the art that various modifications may be made to the present invention without departing from the spirit and scope thereof. The scope of the present invention is to be defined by the following claims and equivalents thereto.

What is claimed:

1. An implantable bone distractor having a longitudinal length extending generally along the direction of distraction, said distractor comprising:

a first base member adapted to be attached to the bone to be distracted;

a second base member adapted to be attached to the bone to be distracted at a position spaced across a separation in the bone from the attachment site of the first base member;

a moving means movably coupling said first base member and said second base member for incremental movement of said second base member relative to said first base member; and An actuating means within said moving means, said actuating means including a shape-memory-effect alloy wire extending substantially along said longitudinal length of said distractor.

2. The distractor of claim 1 wherein said shape-memory-effect alloy wire undergoes Martensitic to Austenitic transformation when electrically energized so that said shape memory-effect alloy wire decreases in length, said decrease in length producing a pulling force that operates said moving means; and said actuating means including a reset spring which applies a bias force to said shape-memory effect alloy to reset said shape-memory-effect alloy wire to its original length during and after Austenitic to Martensitic transformation.

3. The distractor of claim 1 further including connectors attached to said shape-memory-effect alloy wire, wherein said connectors electrically connect said shape-memory-effect alloy wire to electrical leads and said connectors mechanically restrain said shape-memory-effect alloy wire within said distractor.

4. The distractor of claim 1 wherein said moving means includes a ratchet.

5. The distractor of claim 1 wherein said shape-memory-effect alloy wire is an alloy of nickel and titanium.

6. The distractor of claim 1 wherein said actuating means includes a drive spring which is compressed by said shape-memory-effect alloy wire when said shape-memory-effect alloy wire is energized, said drive spring moving said moving means.

7. The distractor of claim 1 further including a rotational adjustment mechanism to rotationally adjust the orientation of said moving means relative to at least one of said base members.

8. The distractor of claim 1 wherein said moving mean is an electromechanical screw comprising:

a) a shaft and screw means;

b) a motion/force transmission means, said motion/force transmission means engaging with said shaft and screw means to impart one-way rotational motion to said shaft and screw means; and c) a housing that contains said motion/force transmission means, said actuating means and a portion of said shaft and screw means.

9. The distractor of claim 8 wherein said motion/force transmission means converts linear motion imparted to it by said actuating means into one-way rotational motion of said shaft and screw means.

10. The distractor means of claim 8 comprising:
   a) at least one pin mounted on shaft and screw means within said housing perpendicular to the length of said shaft and screw means;
   b) a cylindrical cam that slidably engages said at least one pin mounted on shaft and screw means, said cylindrical cam, when angularly secured, causing said shaft and screw means to rotate; and
   c) a clutch that angularly secures said cylindrical cam during rotation of said shaft and screw means, and allows said cylindrical cam to angularly reset after rotation of said shaft and screw means.

11. The distractor of claim 1 wherein said actuating means includes an electromechanical actuator means comprising:
   a) a telescoping housing comprised of a first section and a second section;
   b) at least one rack fixed to said first section; and
   c) a gear train of at least two gears fixed to said second section, said gear train engaged by said at least one rack.

12. The distractor of claim 1 wherein said first base member and said second base member each include bilateral multihole plates, wherein said plates are adapted to be modified by cutting and bending to conform to the contour of the bone at the attachment site.

13. An implantable bone distractor having a length extending generally along the direction of distraction, said distractor comprising:
   a first base member adapted to be attached to the bone to be distracted;
   a second base member adapted to be attached to the bone to be distracted at a position spaced across a separation in the bone from the attaching site of said first base member;
   a moving means movably coupling said first base member and said second base member for incremental movement of said second base member relative to said first base member; and
   an actuating means within said moving means, said actuating means including a shape-memory-effect alloy wire at least partially extending along said length of said distractor, wherein said moving means includes at least one sealed chamber of constant volume that contains said actuating means.

14. The distractor of claim 13 further including connectors attached to said shape-memory-effect alloy wire, wherein said connectors electrically connect said shape-memory-effect alloy wire to electrical leads and said connectors mechanically restrain said shape-memory-effect alloy wire within said distractor.

15. The distractor of claim 13 wherein said moving means includes a clutch.

16. The distractor of claim 13 further including a rotational adjustment mechanism to rotationally adjust the orientation of said moving means relative to at least one of said base members.

17. An implantable bone distractor having a length extending generally along the direction of distraction, said distractor comprising:
   a first base member adapted to be attached to the bone to be distracted;
   a second base member adapted to be attached to the bone to be distracted at a position spaced across a separation in the bone from the attaching site of said first base member;
   a moving means movably coupling said first base member and said second base member for incremental movement of said second base member relative to said first base member; and
   an actuating means within said moving means, said actuating means including a shape-memory-effect alloy wire at least partially extending along said length of said distractor, wherein said moving means includes at least one sealed chamber of constant volume having a hollow lumen extending generally along the direction of distraction, wherein said shape-memory-effect alloy wire extends at least partially within said hollow lumen.

18. An implantable bone distractor comprising:
   a first base member adapted to be attached to the bone to be distracted;
   a second base member adapted to be attached to the bone to be distracted at a position spaced across a separation in the bone from the attachment site of said first base member;
   a moving means movably coupling said first base member and said second base member for incremental movement of said second base member relative to said first base member; and
   an actuating means within said moving means, said actuating means including an electrically energized shape-memory-effect alloy wire and connectors attached to said shape-memory-effect alloy wire, wherein said connectors electrically connect said shape-memory-effect alloy wire to electrical leads and said connectors mechanically secure said shape-memory-effect alloy wire within said distractor.

19. The distractor of claim 18 wherein said connectors are selected from the group consisting of crimps and screw down connectors.

20. The distractor of claim 18 wherein said moving means includes at least one sealed chamber of constant volume that contains said actuating means.

21. The distractor of claim 20 wherein said first base member and said second base member each include bilateral multihole plates, wherein said plates are adapted to be modified by cutting and bending to conform to the contour of the bone at the attachment site.

* * * * *